United States Patent [19]

Berges

[11] 4,159,373
[45] Jun. 26, 1979

[54] 7-ACYL-3-(SULFONIC ACID AND SULFAMOYL SUBSTITUTED TETRAZOLYL THIOMETHYL) CEPHALOSPORINS

[75] Inventor: David A. Berges, Phoenixville, Pa.

[73] Assignee: SmithKline Corporation, Philadelphia, Pa.

[21] Appl. No.: 893,237

[22] Filed: Apr. 4, 1978

Related U.S. Application Data

[63] Continuation-in-part of Ser. No. 759,160, Jan. 13, 1977, Pat. No. 4,093,723, which is a continuation-in-part of Ser. No. 687,792, May 19, 1976, Pat. No. 4,048,311, which is a continuation-in-part of Ser. No. 647,394, Jan. 8, 1976, abandoned, which is a continuation-in-part of Ser. No. 559,609, Mar. 18, 1975, abandoned.

[51] Int. Cl.$^2$ .......................................... C07D 501/36
[52] U.S. Cl. ...................................... 544/26; 424/246
[58] Field of Search ........................................ 544/26

[56] References Cited

U.S. PATENT DOCUMENTS

| | | | |
|---|---|---|---|
| 3,766,176 | 10/1973 | Lemieux et al. | 265/243 C |
| 3,819,623 | 6/1974 | Takano et al. | 544/26 |
| 3,910,899 | 10/1975 | Gottstein et al. | 544/26 |
| 4,068,071 | 1/1978 | Tsushima et al. | 544/27 |
| 4,068,072 | 1/1978 | Tsushima et al. | 544/19 |
| 4,080,498 | 3/1978 | Numata et al. | 544/27 |

*Primary Examiner*—Nicholas S. Rizzo
*Attorney, Agent, or Firm*—Janice E. Williams; William H. Edgerton; Alan D. Lourie

[57] ABSTRACT

The compounds of this invention are cephalosporins having a 3- or 4-aminomethylphenylacetamido substituent at the 7-position and a sulfonic acid substituted tetrazolyl thiomethyl group at the 3-position of the cephem nucleus. The compounds have antibacterial activity.

4 Claims, No Drawings

7-ACYL-3-(SULFONIC ACID AND SULFAMOYL SUBSTITUTED TETRAZOLYL THIOMETHYL) CEPHALOSPORINS

This application is a continuation-in-part of copending application Ser. No. 759,160 filed Jan. 13, 1977, now U.S. Pat. No. 4,093,723 which is a continuation-in-part of Ser. No. 687,792 filed May 19, 1976, now U.S. Pat. No. 4,048,311 which is a continuation-in-part of application Ser. No. 647,394 filed Jan. 8, 1976, now abandoned, which is a continuation-in-part of application Ser. No. 559,609 filed Mar. 18, 1975, now abandoned.

This invention comprises a new series of cephalosporin compounds which have antibacterial activity when administered parenterally and to intermediates for the preparation thereof. In particular, the structures of the biologically active cephalosporin compounds of this invention are characterized by having a sulfonic acid or sulfamoyl substituted tetrazolyl thiomethyl group at the 3-position of the cephem nucleus. Also, this invention extends to methods and compositions for treating certain bacterial infections using these new compounds as well as to certain chemical intermediates and methods for preparing the compounds described hereafter.

The compounds of this invention are represented by the following structural formula:

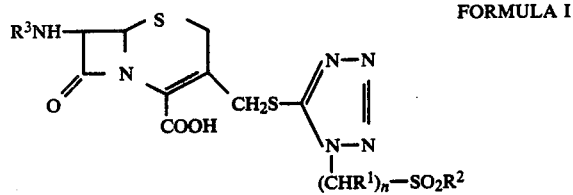

FORMULA I in which:
each individual $R^1$ is hydrogen or lower alkyl;
n is one to ten;
$R^2$ is hydroxy, amino, lower alkylamino or di(lower)alkylamino; and
$R^3$ is an acyl group selected from the group consisting of:

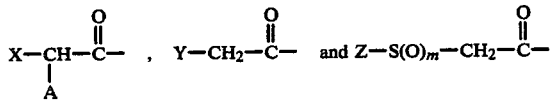

where:
X is thienyl; dihydrophenyl; phenyl; phenyl mono-substituted with hydroxy, hydroxymethyl, formamido, ureido or carboxymethylamino; or 3-fluoro-4-hydroxyphenyl;
A is $NH_2$, OH, COOH or $SO_3H$; or formyloxy when X is phenyl;
Y is thienyl, tetrazolyl, cyano, sydnone or aminomethylphenyl;
Z is methyl, trifluoromethyl, trifluoroethyl, cyanomethyl or pyridyl; and
m is zero to two, or a non-toxic pharmaceutically acceptable salt thereof.

As used herein, the term "lower alkyl" refers to groups having from one to four carbon atoms, preferably methyl and ethyl.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such esters are included within the scope of this invention.

A selected group of compounds of this invention are represented by Formula I where $R^1$ is hydrogen; n is one to five; $R^2$ is hydroxy, amino, lower alkylamino or di(lower)alkylamino;

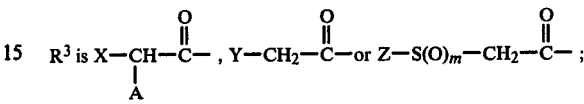

X is thienyl, dihydrophenyl, phenyl, phenyl mono-substituted with hydroxy, hydroxymethyl, formamido, ureido or carboxymethylamino, or 3-fluoro-4-hydroxyphenyl; A is $NH_2$, OH, COOH or $SO_3H$; Y is thienyl, tetrazolyl, cyano, sydnone or aminomethylphenyl; Z is methyl, trifluoromethyl, trifluoroethyl, cyanomethyl or pyridyl and m is zero to two.

Another group of compounds of this invention are represented by Formula I where $R^1$ is hydrogen; n is one to five; $R^2$ is hydroxy, amino, lower alkylamino or di(lower)alkylamino; X is phenyl or hydroxyphenyl; A is $NH_2$ or OH; Y is thienyl; Z is methyl, trifluoromethyl or trifluoroethyl and m is zero to two.

Yet another group are those compounds represented by Formula I where $R^1$ is hydrogen; n is one to five; $R^2$ is hydroxy or amino; X is phenyl or 4-hydroxyphenyl; A is $NH_2$ or OH; Y is thienyl; Z is trifluoromethyl and m is zero.

Examples of representative 7-acyl substituents ($R^3NH-$) of the compounds of Formula I are listed below:
α-hydroxyphenylacetamido
α-aminophenylacetamido
α-amino-4-hydroxyphenylacetamido
trifluoromethylthioacetamido
methylthioacetamido
2,2,2-trifluoroethylsulfinylacetamido
thienylacetamido
tetrazolylacetamido
cyanoacetamido
α-carboxythienylacetamido
α-carboxyphenylacetamido
α-sulfophenylacetamido
methylsulfonylacetamido
cyanomethylthioacetamido
α-amino-4-carboxymethylaminophenylacetamido
α-amino-3-fluoro-4-hydroxyphenylacetamido
3-sydnoneacetamido
4-pyridylthioacetamido
2-aminomethylphenylacetamido.

Representative substituted tetrazolyl groups are the following:
1-sulfomethyltetrazolyl
1-(2-sulfoethyl)tetrazolyl
1-(2-sulfamoylethyl)tetrazolyl
1-(3-sulfopropyl)tetrazolyl
1-(3-sulfamoylpropyl)tetrazolyl
1-(5-sulfopentyl)tetrazolyl
1-(5-sulfamoylpentyl)tetrazolyl.

Some examples of the compounds of this invention are 7-D-mandelamido-3-(1-sulfomethyltetrazol-5-ylthiomethyl)-3-cephem-4-carboxylic acid, 7-D-mandelamido-3-[1-(2-sulfoethyl)tetrazol-5-ylthiomethyl]-3-cephem-4-carboxylic acid, 7-D-mandelamido-3-[1-(5-sulfopentyl)tetrazol-5-ylthiomethyl]-3-cephem-4-carboxylic acid, 7-D-mandelamido-3-[1-(2-sulfamoylethyl)tetrazol-5-ylthiomethyl]-3-cephem-4-carboxylic acid, 7-(2-thienylacetamido)-3-(1-sulfomethyltetrazol-5-ylthiomethyl)-3-cephem-4-carboxylic acid, 7-(2-thienylacetamido)-3-[1-(2-sulfoethyl)tetrazol-5-ylthiomethyl]-3-cephem-4-carboxylic acid, 7-trifluoromethylthioacetamido-3-(1-sulfomethyltetrazol-5-ylthiomethyl)-3-cephem-4-carboxylic acid, 7-(2-thienylacetamido)-3-[1-(2-sulfamoylethyl)tetrazol-5-ylthiomethyl]-3-cephem-4-carboxylic acid and 7-trifluoromethylthioacetamido-3-[1-(2-sulfamoylethyl)tetrazol-5-ylthiomethyl]-3-cephem-4-carboxylic acid.

Cephalosporin derivatives having 7-acyl substituents as defined above are all documented in the prior art. Substitution by a substituted S-heterocyclicthiomethyl group (—CH$_2$SHet) at the 3-position of the cephem nucleus is also known and is disclosed in Netherlands Pat. No. 6916151 where Het is, among others, tetrazolyl substituted with, inter alia, carboxy, carbalkoxy, alkoxyalkylaminocarbonyl and dialkylaminoalkylaminocarbonyl and in Japanese Pat. No. 7205550 where Het includes tetrazolyl substituted with —(CH$_2$)$_n$R$^3$ where n is 0 to 3 and R$^3$ includes alkoxycarbonyl, carboxy, N-alkoxyalkylcarbamoyl and dialkylamino. Recently issued U.S. Pat. No. 3,819,623 discloses cephalosporins bearing a 7-heterocyclicacetamido or 7-heterocyclicthioalkylacetamido group and having in the 3-position, inter alia, thiomethyltetrazolyl substituted with carboxy, alkoxycarbonyl, carboxyalkyl, alkoxycarbonylalkyl and dialkylaminoalkylaminocarbonylalkyl. No compounds containing applicant's 3-(sulfonic acid or sulfamoyl substituted tetrazolyl)thiomethyl moiety disclosed herein are believed to be known to the art.

The compounds of Formula I are prepared by acylating 7-aminocephalosporanic acid with an appropriately protected acylating agent and then displacing the 3-acetoxy group with the desired substituted tetrazole thiol with subsequent removal of the protective group(s). The substituted tetrazole thiols of the formula:

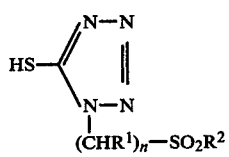

FORMULA II in which:
each individual R$^1$ is hydrogen or lower alkyl;
n is one to ten; and
R$^2$ is hydroxy, amino, lower alkylamino or di(lower)alkylamino,
are also objects of this invention, being important intermediates for producing pharmaceutical end products as described herein.

The carboxylic acid group of the acylating agent is activated by any of the standard methods such as conversion to the mixed anhydride, acid chloride, acid imidazolide or activated ester. In addition, a reagent such as dicyclohexylcarbodiimide can be used provided that the carboxyl group on the cephem nucleus is protected with an easily removable protecting group such as a benzhydryl, t-butyl, trichloroethyl, benzyl, benzyloxymethyl, p-nitrophenyl, p-methoxyphenyl, p-methoxybenzyl or p-nitrobenzyl ester. When A is NH$_2$, the α-amino group of the acylating agent is, preferably, protected prior to acylation with an easily removable protective group known in the art such as t-butoxycarbonyl, trichloroethoxycarbonyl, benzyloxycarbonyl, the methyl acetoacetate adduct or similar groups commonly used in the synthesis of peptides.

Alternatively, the compounds of Formula I are prepared by acylation of an appropriate 7-amino-3-substituted tetrazolylthiomethyl cephalosporin nucleus of Formula III:

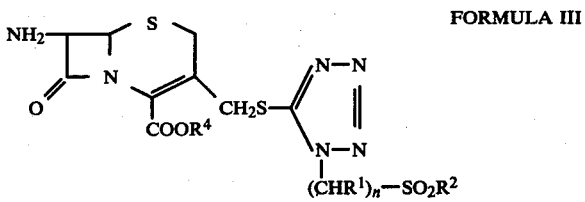

FORMULA III in which:
each individual R$^1$ is hydrogen or lower alkyl;
n is one to ten;
R$^2$ is hydroxy, amino, lower alkylamino or di(lower)alkylamino; and
R$^4$ is hydrogen or a protecting ester group,
with an appropriate acylating agent followed by removal of the protective groups when present.

The compounds of Formula III above are also considered as objects of this invention.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The acylating agents used as starting materials are either known or prepared by known methods.

The 7-amino-3-substituted tetrazolylthiomethyl cephalosporin starting materials of Formula III are prepared from reaction of 7-formamidocephalosporanic acid, prepared by reaction of 7-aminocephalosporanic acid with formic acid and acetic anhydride, and a substituted tetrazole thiol of Formula II followed by treatment with acid such as hydrochloric acid to remove the formyl group.

The substituted tetrazole thiols of Formula II where R$^2$ is hydroxy, lower alkylamino or di(lower)alkylamino are prepared by reaction of an N-alkyl dithiocarbamate, such as methyl 2-sulfoethyldithiocarbamate or methyl 3-(N-t-butylsulfamoylpropyl)dithiocarbamate or its corresponding sodium or potassium salt with an azide such as sodium azide. The N-alkyl dithiocarbamates are prepared by treatment of an aminoalkanesulfonic acid, for example 2-aminoethanesulfonic acid, or an amino(N-alkyl or N,N-dialkyl)sulfonamide such as 3-aminopropane-N-t-butylsulfonamide or its corresponding salt with carbon disulfide and an alkyl halide such as methyl iodide in the presence of a base such as sodium or potassium hydroxide.

The amino(N-alkyl or N,N-dialkyl)sulfonamides are prepared by reaction of an N-alkyl or N,N-dialkylphthalimidoalkylsulfonamide, obtained from treatment of a phthalimidoalkylsulfonyl halide, preferably chloride, with an alkyl- or dialkylamine and then with hydrazine. The phthalimidoalkylsulfonyl halides are known or are prepared as described by Winterbottom et al., *J. Amer. Chem. Soc.* 69:1393 (1947) and Griffin and Hey, *J. Chem. Soc.*, 3334 (1952).

When $R^2$ is amino, the compounds of Formula II are prepared by removal of the N-alkyl group, which also serves as an amine protective group, from the corresponding N-alkylsulfamoylalkyltetrazole-5-thiol, preferably a N-t-butylsulfamoylalkyltetrazole-5-thiol, with, for example, anisole and trifluoroacetic acid.

Certain compounds of this invention are capable of forming salts with, for example, the alkali metals such as sodium or potassium, the alkaline earth metals such as calcium or with the ammonium cation. When A is $NH_2$, the compounds can exist as the zwitterion or as either an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7-acetamido group of Formula I when

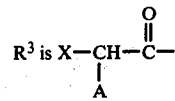

and the potentially asymmetric carbon atom in the tetrazole sidechain, optical isomers will exist. Racemic or resolved products are obtained depending upon whether a racemic or resolved sidechain acid is used as an acylating agent and whether a racemic or resolved tetrazole thiol is used. The resolved sidechain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I have exceptional antibacterial activity against both Gram-positive and Gram-negative organisms. Minimum inhibitory concentrations (MIC's) ranged from 0.2 to <200 μg./ml. in in vitro testing. These results are shown in Table 1 below for representative compounds of Formula I. In vivo mouse protection data are given in Table 2. Compound names corresponding to numbers are given in Table 3.

TABLE 1

| | | | | | | | MIC (μg./ml.) in vitro | | | | | | | |
|---|---|---|---|---|---|---|---|---|---|---|---|---|---|---|
| Compound | S. aureus HH 127 | S. aureus SK 23390 | S. villaluz | Strep. Faecalis HH 34358 | E. coli SK 12140 | E. coli HH 33779 | Kleb. pneumo. SK 4200 | Kleb. pneumo. SK 1200 | Psuedo. sp. HH 63 | Salmonella ATCC 12176 | shigella HH 117 | Entero. aerog. ATCC 13048 | Serra. marc ATCC 13880 | Entero. cloacae HH 31254 | Proteus morgani 179 |
| I | 3.1, 6 | 0.8, 6 | 6.3, 50 | 50, 100 | 0.8, 0.8 | 3.1, 1.6 | 0.8, 0.8 | 0.2, 0.8 | >200, >200 | 0.8, 0.4 | 0.4, 0.4 | 3.1, 13 | 12.5, 13 | 0.8, 3 | 3.1, 3 |
| II | 1.6 | 0.8 | 6.3 | 50 | 0.8 | 1.6 | 0.8 | 0.4 | >200 | 0.8 | 0.4 | 6.3 | 25 | 3.1 | 6.3 |
| III | 1.6 | 0.2 | 3.1 | 12.5 | 0.8 | 1.6 | 1.6 | 0.8 | >200 | 0.8 | 0.2 | 3.1 | 6.3 | 0.8 | 3.1 |
| IV | 3.1 | 0.8 | 12.5 | 50 | 1.6 | 6.3 | 1.6 | 1.6 | >200 | 3.1 | 0.8 | 6.3 | 100 | 0.8 | 3.1 |
| V | 0.8, 0.8 | 0.4, 0.4 | 3.1, 12.5 | 25, 50 | 1.6, 1.6 | 6.3, 6.3 | 1.6, 0.8 | 0.4, 0.4 | >200, >200 | 0.8, 0.8 | 1.6, 1.6 | 12.5, 12.5 | 100, 100 | 1.6, 1.6 | 3.1 |
| VI | 1.6 | 0.8 | 3.1 | 50 | 3.1 | 12.5 | 1.6 | 0.8 | >200 | 0.4 | 3.1 | 25 | 200 | 6.3 | >200, >200 |
| VII | 0.8, 0.8 | 0.8, 0.4 | 50, 15 | 50, 50 | 0.8, 0.8 | 3.1, 1.6 | 0.4, 1.6 | 0.4, 0.2 | >200, >200 | 0.4, 0.2 | 0.8, 0.8 | 6.3, 3.1 | >200, 200 | 3.1, 0.8 | >200, 100 |
| VIII | 0.4 | 0.1 | 1.6 | 6.3 | 0.8 | 1.6 | 1.6 | 0.4 | >200 | 0.8 | 0.4 | 3.1 | 100 | 0.8 | 100 |
| IX | 0.2 | 0.2 | 6.3 | 12.5 | 0.8 | 1.6 | 0.8 | 0.4 | >200 | 0.4 | 0.2 | 1.6 | 200 | 0.8 | >200 |
| X | 1.6 | 1.6 | >200 | 50 | 0.4 | 0.8 | 0.4 | 0.2 | >200 | ≤0.1 | — | 3.1 | 100 | 0.8 | 200 |
| XI | 1.6 | 1.6 | 200 | 25 | 0.2 | 0.4 | ≤0.1 | ≤0.1 | >200 | ≤0.1 | — | 0.8 | 200 | 0.8 | 200 |
| XII | 1.6 | 1.6 | >200 | 50 | 0.8 | 1.6 | 0.8 | 0.4 | >200 | 0.4 | — | 3.1 | 6.3 | 1.6 | 50 |
| XIII | 0.4 | 0.2 | 200 | 6.3 | 0.8 | 0.8 | 0.8 | 0.8 | >200 | 0.8 | — | 1.6 | 50 | 0.8 | 200 |

TABLE 2

| Compound | ED$_{50}$ in vivo (mg./kg.) | | | |
| --- | --- | --- | --- | --- |
| | E. coli 12140 | | Kleb. pneumo. 4200 | |
| | s.c. | p.o. | s.c. | p.o. |
| I | 1.56 | — | 0.28 | — |
| II | 0.58 | 35 | 0.39 | 18.6 |
| III | 0.70 | 25 | 0.68 | 21.5 |
| IV | 18 | >50 | 15.7 | — |
| V | 4 | >50 | 0.26 | — |
| VI | 4.4 | — | 1.56 | — |
| VII | 0.86 | — | 0.24 | — |
| VIII | 1.32 | >50 | 2 | — |
| IX | 1.56 | 44 | — | — |
| X | 1.56 | 50 | 0.64 | — |
| XI | 21.5 | — | — | — |
| XIII | 4 | — | 6.25 | — |

TABLE 3

| Compound Number | Compound Name |
| --- | --- |
| I | 7-D-Mandelamido-3-(1-sulfomethyl-tetrazol-5-ylthiomethyl)-3-cephem-4-carboxylic acid |
| II | 7-D-Mandelamido-3-[1-(2-sulfoethyl)-tetrazol-5-ylthiomethyl]-3-cephem-4-carboxylic acid |
| III | 7-D-Mandelamido-3-[1-(2-sulfamoyl-ethyl)tetrazol-5-ylthiomethyl]-3-cephem-4-carboxylic acid |
| IV | 7-D-Mandelamido-3-[1-(5-sulfopentyl)-tetrazol-5-ylthiomethyl]-3-cephem-4-carboxylic acid |
| V | 7-(2-Thienylacetamido)-3-(1-sulfo-methyltetrazol-5-ylthiomethyl)-3-cephem-4-carboxylic acid |
| VI | 7-(2-Thienylacetamido)-3-[1-2-sulfoethyl)tetrazol-5-ylthiomethyl]-3-cephem-4-carboxylic acid |
| VII | 7-Trifluoromethylthioacetamido-3-(1-sulfomethyltetrazol-5-ylthiomethyl)-3-cephem-4-carboxylic acid |
| VIII | 7-(2-Thienylacetamido)-3-[1-(2-sulfamoyl-ethyl)tetrazol-5-ylthiomethyl]-3-cephem-4-carboxylic acid |
| IX | 7-Trifluoromethylthioacetamido-3-[1-(2-sulfamoylethyl)tetrazol-5-ylthio-methyl]-3-cephem-4-carboxylic acid |
| X | 7-(1-Tetrazolylacetamido)-3-(1-sulfo-methyltetrazol-5-ylthiomethyl)-3-cephem-4-carboxylic acid |
| XI | 7-(o-aminomethylphenylacetamido)-3-(1-sulfomethyltetrazol-5-ylthiomethyl)-3-cephem-4-carboxylic acid |
| XII | 7-Cyanoacetamido-3-(1-sulfomethyltetrazol-5-ylthiomethyl)-3-cephem-4-carboxylic acid |
| XIII | Cefazolin |

In addition, the active compounds of this invention exhibit broad spectrum activity and show advantageously high blood serum levels and half-life values.

Pharmaceutical compositions having antibacterial activity which comprise a pharmaceutical carrier containing an active but non-toxic quantity of a compound of Formula I as well as methods of combatting bacterial infections by administering such a composition to an infected host in a nontoxic amount sufficient to combat such infections are also objects of this invention. The administration may be by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other cephalosporins. The dosage regimen comprises administration, preferably by injection, of an active but nontoxic quantity of a compound of Formula I selected from the dosage unit range of from 100 to 1000 mg. with the total daily dosage regimen being from 400 mg. to 6 g. The precise dosages are dependent upon the age and weight of the subject and on the infection being treated and can be determined by those skilled in the art based on the data disclosed herein compared with that available to the art attained with known cephalosporins.

Also considered within the scope of this invention are the 7α-methoxy analogs of the compounds of Formula I, which compounds are represented by the following structural formula:

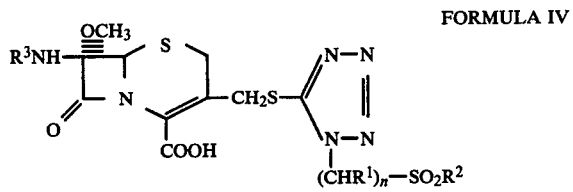

FORMULA IV or a non-toxic pharmaceutically acceptable salt thereof, which $R^1$, $R^2$, $R^3$ and n are as previously defined hereabove.

A selected group of the compounds of Formula IV are those where $R^1$ is hydrogen and n is one to five.

Representative of the compounds of Formula IV are 7α-methoxy-7β-(2-thienylacetamido)-3-(1-sulfomethyl-tetrazol-5-ylthiomethyl)-3-cephem-4-carboxylic acid, 7α-methoxy-7β-trifluoromethylthioacetamido-3-(1-sulfomethyltetrazol-5-ylthiomethyl)-3-cephem-4-carboxylic acid, 7β-D-mandelamido-7α-methoxy-3-(1-sulfomethyltetrazol-5-ylthiomethyl)-3-cephem-4-carboxylic acid, 7α-methoxy-7β-(D-α-aminophenylacetamido)-3-[1-(2-sulfoethyl)tetrazol-5-ylthiomethyl]-3-cephem-4-carboxylic acid and 7β-D-mandelamido-7α-methoxy-3-[1-(2-sulfamoylethyl)tetrazol-5-ylthiomethyl]-3-cephem-4-carboxylic acid.

When $R^2$ is hydroxy the compounds of Formula IV are preferably prepared by displacing the 3-acetoxy group from a 7α-methoxy-7β-acylaminocephalosporanic acid or salt thereof, suitably protected as necessary, with a substituted tetrazole thiol of Formula II where $R^2$ is hydroxy, or a corresponding salt, with subsequent removal of the protective group(s) and conversion of any salts to the corresponding free acids, all as described hereinabove. The 7α-methoxy-7β-acylaminocephalosporanic acids, salts or esters are either known to the art or are prepared by known methods.

When $R^2$ is amino, lower alkylamino or di(lower)alkylamino, the compounds of Formula IV are preferably prepared by acylation of a 7β-amino-7α-methoxy-3-substituted tetrazolylthiomethylcephalosporin nucleus of Formula V:

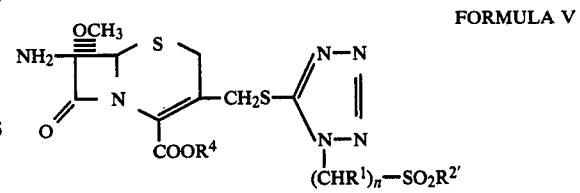

FORMULA V in which $R^1$, $R^4$ and n are as previously defined hereabove and $R^{2'}$ is amino, lower alkylamino or di(lower)alkylamino with an appropriate acylating agent, suitably protected as necessary, by the procedures described above followed by removal of the protective groups, when present, also as described above. The compounds of Formula V are also considered as objects of this invention.

The 7β-amino-7α-methoxy cephalosporin nuclei of Formula V are prepared by reaction of a 7-amino cephalosporin of Formula III where $R^2$ is amino, lower alkylamino or di(lower)alkylamino and $R^4$ is a protecting ester group such as a t-butyl group with 3,5-di-t-butyl-4-hydroxybenzaldehyde with azeotropic removal of water. Subsequent treatment of the product thus formed with lead dioxide and reaction of the oxidized intermediate with methanol followed by cleavage of the imine function with, for example, Girard reagent T (trimethylaminoacetohydrazide chloride) followed by removal of the protective group(s) as desired gives the corresponding compounds of Formula V.

As with the compounds of Formula I, all non-toxic pharmaceutically acceptable salts and all isomers, including separated isomers and mixtures thereof, of the compounds represented by Formula IV are included within the scope of this invention.

The compounds of Formula IV have anti-bacterial activity against both Gram-positive and Gram-negative organisms. They are administered and formulated in the same manner as previously described for the compounds of Formula I.

The following examples illustrate the invention, but are not to be construed as limiting the scope thereof. Temperatures are in degrees Centigrade unless otherwise stated.

EXAMPLE 1

7-D-Mandelamido-3-(1-sulfomethyltetrazol-5-ylthiomethyl)-3-cephem-4-carboxylic acid To a solution of 112 g. (2.0 mol.) of potassium hydroxide and 111 g. (1.0 mol.) of aminomethanesulfonic acid in 250 ml. of water at 25° was added 71 ml. of carbon disulfide. The reaction mixture was stirred for 12 hours and 250 ml. of ethanol was added. The reaction vessel was fitted with a reflux condenser and 62 ml. (1.0 mol.) of methyl iodide was added. When the exothermic reaction cooled to ambient temperature the solid product was collected by filtration. The solid was extracted with hot methanol and the extract was concentrated to give methyl sulfomethyldithiocarbamate as the potassium salt.

A mixture of 45.3 g. (0.19 mol.) of methyl sulfomethyldithiocarbamate potassium salt and 16.9 g. (0.26 mol.) of sodium azide in 425 ml. of water was heated at 80° for 4.75 hours. The reaction mixture was passed through an Amberlite IR-120H ion exchange resin column and eluted with water until the pH of the eluant became 3.5. The eluant was extracted with ether and the aqueous solution was evaporated to dryness to give 1-sulfomethyltetrazole-5-thiol.

1-Sulfomethyltetrazole-5thiol was dissolved in acetone and a 30% solution of sodium 2-ethylhexanoate in isopropanol was added. 1-Sulfomethyltetrazole-5-thiol sodium salt precipitated and was collected by filtration.

A mixture of 27.4 g. (0.062 mol.) of 7-D-mandelamidocephalosporanic acid methanolate, 10.2 g. (0.047 mol.) of 1-sulfomethyltetrazole-5-thiol sodium salt and 9.2 g. (0.109 mol.) of sodium bicarbonate in 300 ml. of water was heated at 70° for one hour. The reaction mixture was cooled (ice bath) and acidified to pH 1.8 with 3 N hydrochloric acid. The mixture was extracted with ethyl acetate, filtered and chromatographed on an Amberlite XAD-8 resin column with water containing increasing amounts of methanol as the eluant to give the title compound.

The title compound was dissolved in methanol and a 5% solution of sodium methoxide in methanol was added until pH 7.0. Addition of ethanol precipitated the product salt which was collected, dissolved in water and lyophilized to give 7-D-mandelamido-3-(1-sulfomethyltetrazol-5-ylthiomethyl)-3-cephem-4-carboxylic acid disodium salt.

$C_{18}H_{16}N_6O_8S_3.2$ Na.1.75 $H_2O$: Calculated: 34.98% C; 3.18% H; 13.59% N; Found: 35.09% C; 3.17% H; 13.27% N.

EXAMPLE 2

7-(D-α-Aminophenylacetamido)-3-(1-sulfomethyltetrazol-5-ylthiomethyl)-3-cephem-4-carboxylic acid A solution of 7.58 g. (0.015 mol.) of 7-(D-α-t-butoxycarbonylaminophenylacetamido)cephalosporanic acid, 1.96 g. (0.01 mol.) of 1-sulfomethyltetrazole-5-thiol and 2.52 g. (0.03 mol.) of sodium bicarbonate in 125 ml. of water is stirred at 60° for five hours while maintaining the pH at 7.0-7.2 by addition of sodium bicarbonate. The mixture is cooled and extracted with ethyl acetate. The aqueous phase is acidified to pH 2.5 with 3 N hydrochloric acid and the acidic solution is extracted again with ethyl acetate. The aqueous phase is brought to pH 7.1 by addition of 5% sodium carbonate solution, then passed through a XAD-4 ion exchange resin column and eluted with water and methanol to give 7-(D-α-t-butoxycarbonylaminophenylacetamido)-3-(1-sulfomethyltetrazol-5-ylthiomethyl)-3-cephem-4-carboxylic acid disodium salt.

7-(D-α-t-butoxycarbonylaminophenylacetamido)-3-(1-sulfomethyltetrazol-5-ylthiomethyl)-3-cephem-4-carboxylic acid disodium salt is stirred at 25° with 25 ml. of trifluoroacetic acid and 25 ml. of 1,3-dimethoxybenzene for 2.25 hours. The mixture is evaporated to dryness, ether is added to the residue and the precipitate is collected, washed with ether, stirred in acetonitrile for two hours, then collected and dried in vacuo to give the title compound.

EXAMPLE 3

7-D-Mandelamido-3-[1-(2-sulfamoylethyl)tetrazol-5-ylthiomethyl]-3-cephem-4-carboxylic acid A solution of 2.73 g. (0.01 mol.) of 2-phthalimidoethanesulfonyl chloride in 20 ml. of chloroform was added dropwise to a solution of 2.19 g. (0.03 mol.) of t-butylamine in 20 ml. of chloroform at 5°. The reaction mixture was warmed to ambient temperature and stirred for three hours. The precipitate was removed by filtration and the filtrate was evaporated to dryness to give a residue which was purified by chromatography on silica with 19:1 chloroform-methanol as eluant to give 2-N-t-butylphthalimidoethanesulfonamide.

2-N-t-Butylphthalimidoethanesulfonamide (2.10 g., 6.78 mmol.) was suspended in 20 ml. of ethanol and 0.344 g. of hydrazine hydrate was added. The reaction mixture was refluxed for three hours, then evaporated to dryness. The residue was suspended in 45 ml. of water and acidified to pH 3.0 by addition of dilute hydrochloric acid. The acid solution was filtered and the filtrate evaporated to dryness to give 2-aminoethane-N-t-butylsulfonamide hydrochloride.

2-Aminoethane-N-t-butylsulfonamide hydrochloride (1.25 g., 5.78 mmol.) was added a solution of 1.17 g. (11.56 mmol.) of triethylamine in 20 ml. of ethanol. Carbon disulfide (0.44 g., 5.78 mmol.) was added, the mixture was stirred at 25° for 1.5 hours, then 0.82 g. (5.78 mmol.) of methyl iodide in 5 ml. of ethanol was added and the resulting mixture was stirred for 1.5 hours. The mixture was evaporated to dryness and the residue was dissolved in water and acidified to pH 2.0 with dilute hydrochloric acid. The aqueous mixture was extracted with ethyl acetate and the extract was dried (MgSO$_4$) and evaporated to dryness to give methyl 2-(N-t-butylsulfamoyl)-ethyldithiocarbamate.

Methyl 2-(N-t-butylsulfamoyl)ethyldithiocarbamate was treated with sodium azide as described in the procedure of Example 1 for 35 minutes to give 1-(2-N-t-butylsulfamoylethyl)tetrazole-5-thiol.

1-(2-N-t-Butylsulfamoylethyl)tetrazole-5-thiol (1.0 g.) was suspended in 10 ml. of anisole and 20 ml. of trifluoroacetic acid is added. The solution was heated at 56° for 3.5 hours, then cooled. The precipitate was collected by filtration and washed with petroleum ether to give 1-(2-sulfamoylethyl)tetrazole-5-thiol.

A solution of 0.210 g. (2.5 mmol.) of sodium bicarbonate in 5 ml. of water was added to a suspension of 0.272 g. (1 mmol.) of 7-aminocephalosporanic acid in 5 ml. of water and 2.5 ml. of acetone at 15°. The solution was heated to 45°, a solution of 0.314 g. (1.5 mmol.) of 1-(2-sulfamoylethyl)tetrazole-5-thiol in 10 ml. of acetone was added and the reaction mixture was refluxed for two hours while maintaining the pH at 7.4–7.6 by addition of aqueous sodium bicarbonate solution. The mixture was cooled and acidified to pH 4.0 with dilute hydrochloric acid. The precipitate was collected by filtration to give 7-amino-3-[1-(2-sulfamoylethyl)tetrazol-5-ylthiomethyl]-3-cephem-4-carboxylic acid.

To a solution of 1.26 g. (15 mmol.) of sodium bicarbonate in 75 ml. of acetone and 50 ml. of water at 5° was added 2.1 g. (5 mmol.) of 7-amino-3-[1-(2-sulfamoylethyl)tetrazol-5-ylthiomethyl]-3-cephem-4-carboxylic acid. The solution was cooled to −10° and a solution of 1.55 g. (5.5 mmol.) of D-O-dichloroacetylmandeloyl chloride in 25 ml. of acetone was added. The reaction mixture was stirred for 30 minutes in the cold while maintaining the pH at 7.2 by addition of aqueous sodium bicarbonate, then for 1.5 hours at 25°. The mixture was extracted with ether and the aqueous phase was brought to pH 9.3 with 5% sodium carbonate and stirred for 1.5 hours at 25°. The aqueous mixture was extracted with ether, the pH adjusted to 4.5 and the solution was again extracted with ether. The aqueous phase was acidified to pH 1.5 with dilute hydrochloric acid and it was extracted with ethyl acetate. Evaporation of the extract to dryness gave a solid which was suspended in ethyl acetate and filtered. The filtrate was diluted with ether and petroleum ether to precipitate the title compound.

EXAMPLE 4

7-D-Mandelamido-3-[1-(2-N-t-butylsulfamoylethyl)tetrazol-5-ylthiomethyl]-3-cephem-4-carboxylic acid When an equivalent amount of 1-(2-N-t-butylsulfamoylethyl)tetrazol-5-thiol is reacted with 7-aminocephalosporanic acid as described in Example 3, 7-amino-3-[1-(2-N-t-butylsulfamoylethyl)tetrazol-5-ylthiomethyl]-3-cephem-4-carboxylic acid is obtained.

Acylation of 7-amino-3-[1-(2-N-t-butylsulfamoylethyl)tetrazol-5-ylthiomethyl]-3-cephem-4-carboxylic acid with D-O-dichloroacetylmandeloyl chloride according to the procedure of Example 3 gives the title compound.

EXAMPLE 5

7-D-Mandelamido-3-[1-(2-N-methylsulfamoylethyl)tetrazol-5-ylthiomethyl]-3-cephem-4-carboxylic acid Use of methylamine in the reaction with 2-phthalimidoethanesulfonyl chloride described in Example 3, followed by the subsequent synthetic steps described therein gives 1-(2-N-methylsulfamoylethyl)tetrazol-5-thiol.

When 1-(2-N-methylsulfamoylethyl)tetrazol-5-thiol is reacted with 7-aminocephalosporanic acid as described in Example 3 and the product 7-amino-3-[1-(2-N-methylsulfamoylethyl)tetrazol-5-ylthiomethyl]-3-cephem-4-carboxylic acid is acylated with D-O-dichloroacetylmandeloyl chloride as described therein, the title compound is obtained.

EXAMPLE 6

7-(D-α-Amino-4-hydroxyphenylacetamido)-3-[1-(2-sulfamoylethyl)tetrazol-5-ylthiomethyl]-3-cephem-4-carboxylic acid A solution of 7.82 g. (0.015 mol.) of 7-(D-α-t-butoxycarbonyl-4-hydroxyphenylacetamido)cephalosporanic acid, 4.6 g. (0.022 mol.) of 1-(2-sulfamoylethyl)tetrazole-5-thiol and sodium bicarbonate are reacted according to the procedure described in Example 2. After cooling, the reaction mixture is extracted with ethyl acetate. Fresh ethyl acetate is added to the aqueous phase and it is acidified with stirring to pH 2.8 with 6 N sulfuric acid. The layers are separated and the aqueous phase is again extracted with ethyl acetate. The combined extracts are washed with water, dried (MgSO$_4$) and the solvent evaporated to give 7-(D-α-t-butoxycarbonyl-4-hydroxyphenylacetamido)-3-[1-(2-sulfamoylethyl)tetrazol-5-ylthiomethyl]-3-cephem-4-carboxylic acid.

7-(D-α-t-Butoxycarbonyl-4-hydroxyphenylacetamido)-3-[1-(2-sulfamoylethyl)tetrazol-5-ylthiomethyl]-3-cephem-4-carboxylic acid is treated with trifluoroacetic acid as described in Example 2 to give the title compound.

EXAMPLE 7

7-D-Mandelamido-3-[1-(2-sulfoethyl)tetrazol-5-ylthiomethyl]-3-cephem-4-carboxylic acid 2-Aminoethanesulfonic acid (50 g., 0.4 mol.) was added to a solution of 45 g. (0.8 mol.) of potassium hydroxide in 100 ml. of water at 25°. Carbon disulfide (24.4 ml., 0.4 mol.) was added and the reaction mixture was refluxed for 2.5 hours. Ethanol was added to the warm solution, the mixture was cooled to ambient temperature, 57 g. (0.4 mol.) of methyl iodide was added and the resulting mixture was stirred for 1.5 hours. The mixture was evaporated in vacuo and the residue recrystallized from hot ethanol containing 3% water to give methyl 2-sulfoethyldithiocarbamate potassium salt.

A mixture of 21.5 g. (0.087 mol.) of methyl 2-sulfoethyldithiocarbamate potassium salt (0.5 hydrate) and 7.16 g. (0.11 mol.) of sodium azide in 200 ml. of water was refluxed for two hours. The solution was cooled to 25° and extracted with ethyl acetate. The aqueous phase was treated with Amberlite IR-120H resin, washed with ether and evaporated to give an oil. The oil was dissolved in acetone, the solution was filterd and the filtrate was evaporated to dryness to give 1-(2-sulfoethyl)-tetrazole-5-thiol. The thiol was dissolved in isopropanol, cyclohexylamine was added until pH 8–9 and acetonitrile was added to give 1-(2-sulfoethyl)tetrazole-5-thiol as the di-cyclohexylamine salt.

1-(2-Sulfoethyl)tetrazole-5-thiol di-cyclohexylamine salt was dissolved in water and treated with Amberlite IR-12OH resin to give 1-(2-sulfoethyl)tetrazole-5-thiol.

To a solution of 2.1 g. (0.01 mol.) of 1-(2-sulfoethyl)-tetrazole-5-thiol in 100 ml. of water was added 6.4 g. (0.015 mol.) of 7-D-mandelamidocephalosporanic acid sodium salt and 1.68 g. (0.02 mol.) of sodium bicarbonate. The mixture was stirred at 70° for 2.5 hours then cooled and acidified to pH 1.8 with 3 N hydrochloric acid. The acid solution was extracted with ethyl acetate and ether, acidified to pH 0.9 and chromatographed on a XAD-8 resin column with water as eluant to give the title compound.

The title compound was converted to the corresponding disodium salt by treatment with sodium methoxide as described in the procedure of Example 1.

$C_{19}H_{18}N_6O_8S_3.2$ Na.2 $H_2O$: Calculated: 35.85% C; 3.48% H; 13.20% N; Found: 36.21% C; 3.29% H; 12.96% N;

EXAMPLE 8

7-D-Mandelamido-3-(1-sulfamoylmethyltetrazol-5-ylthiomethyl)-3-cephem-4-carboxylic acid A suspension of 15.1 g. (0.136 mol.) of aminomethanesulfonic acid and 14.2 g. (0.145 mol.) of anhydrous potassium acetate in 48 ml. of acetic acid is refluxed for ten minutes. Phthalic anhydride (21.4 g., 0.145 mol.) is then added and the resulting mixture is refluxed for 2.5 hours. The product is collected by filtration and washed with acetic acid and ethanol to give phthalimidomethanesulfonic acid potassium salt.

To 41.7 g. (0.15 mol.) of phthalimidomethanesulfonic acid potassium salt in 220 ml. of dry benzene is added 22.5 g. (0.132 mol.) of phosphorus pentachloride. The reaction mixture is refluxed on a steam bath for one hour, then an additional 22.5 g. of phosphorus pentachloride is added and heating is continued for 1.5 hours. The reaction mixture is evaporated to dryness, crushed ice is added to the residue and the slurry is filtered. The product is washed with water to give phthalimidomethanesulfonyl chloride.

When phthalimidomethanesulfonyl chloride is substituted in the procedure of Example 3 for 2-phthalimidoethanesulfonyl chloride, N-t-butylphthalimidomethanesulfonamide is prepared which is converted to 1-N-t-butylsulfamoyl methyltetrazole-5-thiol as described therein. Treatment of 1-N-t-butylsulfamoylmethyltetrazole-5-thiol with trifluoroacetic acid as described in Example 3 gives 1-sulfamoylmethyltetrazole-5-thiol.

Reaction of 1-sulfamoylmethyltetrazole-5-thiol with 7-aminocephalosporanic acid and treatment of the product 7-amino-3-(1-sulfamoylmethyltetrazol-5-ylthiomethyl)-3-cephem-4-carboxylic acid with D-O-dichloroacetylmandeloyl chloride as described in Example 3 gives the title compound.

EXAMPLE 9

7-(D-α-Amino-4-hydroxyphenylacetamido)-3-[1-(2-N,N-dimethylsulfamoylethyl)tetrazol-5-ylthiomethyl]-3-cephem-4-carboxylic acid 1-(2-N,N-Dimethylsulfamoylethyl)tetrazole-5-thiol is prepared from reaction of dimethylamine and 2-phthalimidoethanesulfonyl chloride followed by conversion of the product thus obtained to the tetrazole thiol by the reaction sequence described in the procedure of Example 3.

When 1-(2-N,N-dimethylsulfamoylethyl)tetrazole-5-thiol is reacted with 7-(D-α-t-butoxycarbonyl-4-hydroxyphenylacetamido)cephalorsporanic acid as described in Example 6 and the product is de-blocked as described above, the title compound is obtained.

EXAMPLE 10

7-D-Mandelamido-3-[1-(3-sulfopropyl)tetrazol-5-ylthiomethyl]-3-cephem-4-carboxylic acid When an equivalent amount of 3-aminopropanesulfonic acid was substituted in the procedure of Example 7 for 2-aminoethanesulfonic acid, methyl 3-sulfopropyldithiocarbamate potassium salt was prepared.

Reaction of methyl 3-sulfopropyldithiocarbamate potassium salt with sodium azide as described in Example 7 gave 1-(3-sulfopropyl)tetrazole-5-thiol.

Substitution of an equivalent amount of 1-(3-sulfopropyl)tetrazole-5-thiol in the procedure of Example 7 in place of 1-(2-sulfoethyl)tetrazole-5-thiol in the reaction with 7-D-mandelamidocephalosporanic acid sodium salt gives the title compound.

The title compound is converted to the corresponding sodium salt as described in the procedure of Example 1.

EXAMPLE 11

7-D-Mandelamido-3-[1-(3-sulfamoylpropyl)tetrazol-5-ylthiomethyl]-3-cephem-4-carboxylic acid When 3-phthalimidopropanesulfonyl chloride is substituted in the procedure of Example 3 for 2-phthalimidoethanesulfonyl chloride, 3-N-t-butylphthalimidopropanesulfonamide is prepared, which is converted to 1-(3-N-t-butylsulfamoylpropyl)tetrazole-5-thiol as described therein. Treatment of 1-(3-N-t-butylsulfamoylpropyl)-tetrazole-5-thiol with trifluoroacetic acid as described in Example 3 gives 1-(3-sulfamoylpropyl)tetrazole-5-thiol.

Reaction of 1-(3-sulfamoylpropyl)tetrazole-5-thiol with 7-aminocephalosporanic acid and treatment of the resulting 7-amino-3-[1-(3-sulfamoylpropyl)tetrazol-5-ylthiomethyl]-3-cephem-4-carboxylic acid with D-O-dichloroacetylmandeloyl chloride as described in Example 3 gives the title compound.

EXAMPLE 12

7-D-Mandelamido-3-[1-(5-sulfopentyl)tetrazol-5-ylthiomethyl]-3-cephem-4-carboxylic acid Substitution of an equivalent amount of 5-aminopentanesulfonic acid in the procedure of Example 7 for 2-aminoethanesulfonic acid gave methyl 5-sulfopentyldithiocarbamate potassium salt.

Reaction of methyl 5-sulfopentyldithiocarbamate potassium salt with sodium azide as described in Example 7 gave 1-(5-sulfopentyl)tetrazole-5-thiol.

A mixture of 4.55 g. (0.010 mol.) of 7-D-mandelamidocephalosporanic acid sodium salt and 3.25 g. (0.011 mol.) of 1-(5-sulfopentyl)tetrazole-5-thiol disodium salt, prepared as previously described, in 80 ml. of water at pH 7.2 (adjusted by addition of sodium bicarbonate) was heated at 65° for 4.5 hours. The reaction mixture was cooled, acidified to pH 1.6 with 3 N hydrochloric acid and extracted with ethyl acetate. The pH of the aqueous phase was brought to 7.0 by addition of sodium bicarbonate and the solution was chromatographed on a XAD-4 resin column eluting with water and then methanol. The product was dissolved in methanol and ethanol was added to the solution to precipitate the title compound as its disodium salt.

$C_{22}H_{24}N_6O_8S_3 \cdot 2\text{ Na} \cdot 1.5\text{ H}_2O \cdot 0.75\text{ C}_2H_6O$: Calculated: 40.08% C; 4.50% H; 11.93% N; 13.65% S; Found: 40.01% C; 4.20% H; 10.71% N; 13.54% S.

7-D-Mandelamido-3-[1-(5-sulfopentyl)tetrazol-5-ylthiomethyl]-3-cephem-4-carboxylic acid disodium salt is converted to the title compound as described herein.

EXAMPLE 13

7-D-Mandelamido-3-[1-(5-sulfamoylpentyl)tetrazol-5-ylthiomethyl]-3-cephem-4-carboxylic acid Use of 5-aminopentanesulfonic acid in the procedure of Example 8 in place of aminomethanesulfonic acid followed by reaction of the product thus obtained with phosphorus pentachloride gives 5-phthalimidopentanesulfonyl chloride.

When 5-phthalimidopentanesulfonyl chloride is used as a starting material in the sequence described in Example 3, 1-(5-N-t-butylsulfamoylpentyl)tetrazole-5-thiol is obtained. Treatment of 1-(5-N-t-butylsulfamoylpentyl)tetrazole-5-thiol with trifluoroacetic acid as described above gives 1-(5-sulfamoylpentyl)tetrazole-5-thiol.

Reaction of 1-(5-sulfamoylpentyl)tetrazole-5-thiol with 7-aminocephalosporanic acid and treatment of the resulting 7-amino-3-[1-(5-sulfamoylpentyl)tetrazol-5-ylthiomethyl]-3-cephem-4-carboxylic acid with D-O-dichloroacetylmandeloyl chloride as described in Example 3 gives the title compound.

EXAMPLE 14

7-Trifluoromethylthioacetamido-3-(1-sulfomethyltetrazol-5-ylthiomethyl)-3-cephem-4-carboxylic acid A solution of 2.18 g. (10.0 mmol.) of 1-sulfomethyltetrazole-5-thiol sodium salt, prepared as described above, 0.840 g. of sodium bicarbonate and 5.45 g. (12.5 mmol.) of 7-trifluoromethylthioacetamidocephalosporanic acid sodium salt in 60 ml. of water was stirred at 70°–75° for five hours while maintaining the pH at 6.8 by addition of 5% aqueous sodium carbonate solution. The reaction mixture was cooled and diluted with water. Ethyl acetate was added and the mixture was acidified to pH 2.0 with 6 N hydrochloric acid. The aqueous phase was extracted with ethyl acetate then brought to pH 6.8 by addition of sodium bicarbonate and chromatographed on XAD-4 resin with water and methanol as eluants. The product-containing fractions were evaporated to dryness to give a residue which was dissolved in water and lyophilized to give the title compound as the disodium salt.

$C_{13}H_{11}F_3N_6O_7S_4 \cdot 2\text{ Na} \cdot 2.25\text{ H}_2O$: Calculated: 24.59% C; 2.46% H; 13.23% N; Found: 24.54% C; 2.18% H; 12.85% N.

An aqueous solution of 7-trifluoromethylthioacetamido-3-(1-sulfomethyltetrazol-5-ylthiomethyl)-3-cephem-4-carboxylic acid disodium salt is treated with Amberlite IR-120H ion exchange resin as described above to give the title compound.

EXAMPLE 15

7-Trifluoromethylthioacetamido-3-[1-(3-sulfamoylpropyl)tetrazol-5-ylthiomethyl]-3-cephem-4-carboxylic acid 7-Trifluoromethylthioacetamido-3-[1-(3-sulfamoylpropyl)tetrazol-5-ylthiomethyl]-3-cephem-4-carboxylic acid sodium salt is prepared by substitution of an equivalent amount of 1-(3-sulfamoylpropyl)tetrazole-5-thiol sodium salt, prepared as described above, in the procedure of Example 14.

The title compound is obtained from the salt as described above.

EXAMPLE 16

7-Trifluoromethylthioacetamido-3-[1-(2-sulfamoylethyl)tetrazol-5-ylthiomethyl]-3-cephem-4-carboxylic acid A mixture of 2.18 g. (5 mmol.) of 7-trifluoromethylthioacetamidocephalosporanic acid sodium salt and 1.75 g. (8 mmol.) of 1-(2-sulfamoylethyl)tetrazole-5-thiol in 50 ml. of water maintained at pH 7.0 by addition of sodium bicarbonate was heated at 60°–70° for three hours. The reaction mixture was cooled, acidified to pH 3.5 and extracted with ethyl acetate. The extract was washed with water, dried (MgSO₄) and evaporated to dryness to give a residue which was dissolved in ethyl acetate. Ether was added, the solution was filtered, petroleum ether was added to the filtrate and the resulting precipitate was collected by filtration and dissolved in methanol. A 5% solution of sodium methoxide in methanol was added to the methanol solution until pH 7.1. Ether was added and the precipitate was collected and dried in vacuo to give 7-trifluoromethylthioacetamido-3-[1-(2-sulfamoylethyl)tetrazol-5-ylthiomethyl]-3-cephem-4-carboxylic acid sodium salt.

7-Trifluoromethylthioacetamido-3-[1-(2-sulfamoylethyl)tetrazol-5-ylthiomethyl]-3-cephem-4-carboxylic acid sodium salt is converted to the title compound by methods described above.

EXAMPLE 17

7-D-Mandelamido-3-[1-(10-sulfodecyl)tetrazol-5-ylthiomethyl]-3-cephem-4-carboxylic acid A suspension of 56 g. (1.0 mol.) of potassium hydroxide and 118.7 g. (0.5 mol.) of 10-aminodecanesulfonic acid in 170 ml. of water is stirred for 30 minutes at 25°, then 40 g. (0.52 mol.) of carbon disulfide and 80 ml. of ethanol are added and the reaction mixture is stirred at 25° for 12 hours. The mixture is refluxed gently for two hours and cooled. Methyl iodide (71 g., 0.3 mol.) and 130 ml. of ethanol are added to the mixture and it is stirred at 25° for 12 hours. The mixture is evaporated to remove the ethanol and the solid residue is collected by filtration to give methyl 10-sulfodecyldithiocarbamate.

Methyl 10-sulfodecyldithiocarbamate (31.4 g., 0.096 mol.) is reacted with 6.5 g. (0.1 mol.) of sodium azide as described above to give 1-(10-sulfodecyl)tetrazole-5-thiol.

1-(10-Sulfodecyl)tetrazole-5-thiol (4.84 g., 15 mmol.) is slowly added to a solution of 3.36 g. (40 mmol.) of sodium bicarbonate in 100 ml. of water. 7-D-Mandelamidocephalosporanic acid (4.20 g., 10 mmol.) is then added and the mixture is heated at 65° for 3.5 hours. The mixture is filtered, the filtrate is extracted with ethyl acetate and the aqueous layer is acidified to pH 4 and extracted again with ethyl acetate. The extract is dried (MgSO4) and evaporated to dryness to give the title compound.

EXAMPLE 18

7-D-Mandelamido-3-[1-(10-sulfamoyldecyl)tetrazol-5-ylthiomethyl]-3-cephem-4-carboxylic acid Use of 10-aminodecanesulfonic acid in the procedure of Example 8 in place of aminomethanesulfonic acid followed by reaction of the product thus obtained with phosphorus pentachloride gives 10-phthalimidodecanesulfonyl chloride.

When 10-phthalimidodecanesulfonyl chloride is used as a starting material in the sequence described in Example 3, 1-(10-N-t-butylsulfamoyldecyl)tetrazole-5-thiol is obtained. Treatment of 1-(10-N-t-butylsulfamoyldecyl)tetrazole-5-thiol with trifluoroacetic acid gives 1-(10-sulfamoyldecyl)tetrazole-5-thiol.

Reaction of 1-(10-sulfamoyldecyl)tetrazole-5-thiol with 7-aminocephalosporanic acid and treatment of the resulting 7-amino-3-[1-(10-sulfamoyldecyl)tetrazol-5-ylthiomethyl]-3-cephem-4-carboxylic acid with D-O-dichloroacetylmandeloyl chloride as described in Example 3 gives the title compound.

EXAMPLE 19

7-D-Mandelamido-3-[1-(2-sulfo-1-methylethyl)tetrazol-5-ylthiomethyl]-3-cephem-4-carboxylic acid Substitution of an equivalent amount of 2-aminopropanesulfonic acid in the procedure of Example 7 for 2-aminoethanesulfonic acid gives methyl (2-sulfo-1-methyl)ethyldithiocarbamate potassium salt.

Treatment of methyl (2-sulfo-1-methyl)ethyldithiocarbamate potassium salt with sodium azide also as described in Example 7 gives 1-(2-sulfo-1-methylethyl)-tetrazole-5-thiol.

7-D-Mandelamidocephalosporanic acid and 1-(2-sulfo-1-methylethyl)tetrazole-5-thiol are reacted in the presence of excess sodium bicarbonate as described in Example 7 to give the title compound.

EXAMPLE 20

When an equivalent amount of an aminosulfonic acid listed below:
2-aminobutanesulfonic acid
1-amino-2-methylpropanesulfonic acid
1-amino-3-methylbutanesulfonic acid
is used in the procedure of Example 7 in place of 2-aminomethanesulfonic acid and the resulting dithiocarbamates are treated with sodium azide as described therein, the following substituted tetrazole thiols are obtained:
1-(1-sulfomethylpropyl)tetrazole-5-thiol
1-(2-methyl-1-sulfopropyl)tetrazole-5-thiol
1-(3-methyl-1-sulfobutyl)tetrazole-5-thiol.

Reaction of a tetrazole thiol listed above with 7-D-mandelamidocephalosporanic acid as described hereinabove gives the following compounds of this invention:
7-D-mandelamido-3-[1-(1-sulfomethylpropyl)tetrazol-5-ylthiomethyl]-3-cephem-4-carboxylic acid
7-D-mandelamido-3-[1-(2-methyl-1-sulfopropyl)tetrazol-5-ylthiomethyl]-3-cephem-4-carboxylic acid
7-D-mandelamido-3-[1-(3methyl-1-sulfobutyl)tetrazol-5-ylthiomethyl]-3-cephem-4-carboxylic acid.

Likewise, reaction of a substituted tetrazole thiol listed above with 7-(D-α-t-butoxycarbonyl-4-hydroxyphenylacetamido)cephalosporanic acid or 7-trifluoromethylthioacetamidocephalosporanic acid according to the procedures described herein with subsequent removal of the protective groups as necessary, gives the corresponding 7-(D-α-amino-4-hydroxyphenylacetamido)-3-(sulfoalkyltetrazol-5-ylthiomethyl)-3-cephem-4-carboxylic acids and 7-trifluoromethylthioacetamido-3-(sulfoalkyltetrazol-5-ylthiomethyl)-3-cephem-4-carboxylic acids.

EXAMPLE 21

When an aminosulfonic acid listed below:
2-aminopropanesulfonic acid
2-aminobutanesulfonic acid
1-amino-2-methylpropanesulfonic acid
1-amino-3-methylbutanesulfonic acid
is substituted as a starting material in the procedure of Example 8 for aminomethanesulfonic acid, the subsequent steps described therein and in Example 3 are carried out and the resulting N-t-butyl sulfamoyl tetrazoles are treated with trifluoroacetic acid as described therein, the following substituted tetrazole thiols are obtained:
1-(1-methyl-2-sulfamoylethyl)tetrazole-5-thiol
1-(1-sulfamoylmethylpropyl)tetrazole-5-thiol
1-(2-methyl-1-sulfamoylpropyl)tetrazole-5-thiol
1-(3-methyl-1-sulfamoylbutyl)tetrazole-5-thiol
1-(3-methyl-1-sulfamoylbutyl)tetrazole-5-thiol.

Reaction of a tetrazole thiol listed above with 7-aminocephalosporanic acid followed by treatment of the resulting 7-amino-3-(sulfamoylalkyl tetrazole-5-ylthiomethyl)-3-cephem-4-carboxylic acid with D-O-dichloroacetylmandeloyl chloride as described in Example 3 gives the compounds of this invention listed below:
7-D-mandelamido-3-[1-(1-methyl-2-sulfamoylethyl)tetrazol-5-ylthiomethyl]-3-cephem-4-carboxylic acid
7-D-mandelamido-3-[1-(1-sulfamoylmethylpropyl)tetrazol-5-ylthiomethyl]-3-cephem-4-carboxylic acid
7-D-mandelamido-3-[1-(2-methyl-1-sulfamoylpropyl)-tetrazol-5-ylthiomethyl]-3-cephem-4-carboxylic acid
7-D-mandelamido-3-[1-(3-methyl-1-sulfamoylbutyl)tetrazol-5-ylthiomethyl]-3-cephem-4-carboxylic acid.

EXAMPLE 22

Reaction of the N-t-butoxycarbonyl derivative of the following cephalosporanic acids:
7-(α-amino-4-formamidophenylacetamido)cephalosporanic acid
7-(α-amino-3-formamidophenylacetamido)cephalosporanic acid
7-(α-amino-4-ureidophenylacetamido)cephalosporanic acid
7-(α-amino-3-ureidophenylacetamidocephalosporanic acid
7-(α-amino-4-hydroxymethylphenylphenylacetamido)-cephalosporanic acid
7-(α-amino-1,4-cyclohexadienylacetamido)cephalosporanic acid
7-(α-amino-3-fluoro-4-hydroxyphenylacetamido)cephalosporanic acid
with 1-(2-sulfamoylethyl9tetrazole-5-thiol as described in the procedure of Example 2 followed by removal of the protective group as described therein gives the following compounds of this invention:

7-(α-amino-4-formamidophenylacetamido)-3-[1-(2-sulfamoylethyl)tetrazol-5-ylthiomethyl]-3-cephem-4-carboxylic acid 7-(α-amino-3-formamidophenylacetamido)-3-[1-(2-sulfamoylethyl)tetrazol-5-ylthiomethyl]-3-cephem-4-carboxylic acid 7-(α-amino-4-ureidophenylacetamido)-3-[1-(2-sulfamoylethyl)tetrazol-5-ylthiomethyl]-3-cephem-4-carboxylic acid 7-(α-amino-3-ureidophenylacetamido)-3-[1-(2-sulfamoylethyl)tetrazol-5-ylthiomethyl]-3-cephem-4-carboxylic acid 7-(α-amino-4-hydroxymethylphenylacetamido)-3-[1-(2-sulfamoylethyl)tetrazol-5-ylthiomethyl]-3-cephem-4-carboxylic acid 7-(α-amino-1,4-cyclohexadienylacetaido)-3-[1-(2-sulfamoylethyl)tetrazol-5-ylthiomethyl]-3-cephem-4-carboxylic acid 7-(α-amino-3-fluoro-4-hydroxyphenylacetamido)-3-[1-(2-sulfamoylethyl)tetrazol-5-ylthiomethyl]-3-cephem-4-carboxylic acid.

By similar procedures described hereinabove, 7-(α-amino substituted phenylacetamido)-3-[1-(2-sulfoethyl)-tetrazol-5-ylthiomethyl]-3-cephem-4-carboxylic acids are prepared by reaction of the N-t-butoxycarbonyl derivative of the cephalosporanic acids listed above with 1-(2-sulfoethyl)tetrazole-5-thiol followed by removal of the protective group as previously described.

EXAMPLE 23

7-(4-Hydroxymandelamido)-3-[1-(2-sulfamoylethyl)-tetrazol-5-ylthiomethyl]-3-cephem-4-carboxylic acid is prepared by reaction of 7-(4-hydroxymandelamido)-cephalosporanic acid and 1-(2-sulfamoylethyl)tetrazole-5-thiol as described in the procedure of Example 3.

Likewise, when 7-(4-hydroxymandelamido)cephalosporanic acid sodium salt is substituted in the procedure of Example 7 for 7-D-mandelamidocephalosporanic acid sodium salt, 7-(4-hydroxymandelamido)-3-[1-(2-sulfoethyl)-tetrazol-5-ylthiomethyl]-3-cephem-4-carboxylic acid is obtained.

EXAMPLE 24

Reaction of a cephalosporanic acid listed below:
7-(α-hydroxy-2-thienylacetamido)cephalosporanic acid
7-(α-carboxy-2-thienylacetamido)cephalosporanic acid
7-(α-sulfophenylacetamido)cephalosporanic acid
with 1-(2-sulfamoylethyl)tetrazole-5-thiol or 1-(2-sulfoethyl)tetrazole-5-thiol as described hereinabove gives the following compounds of this invention:
7-(α-hydroxy-2-thienylacetamido)-3-[1-(2-sulfamoylethyl)tetrazol-5-ylthiomethyl]-3-cephem-4-carboxylic acid
7-(α-hydroxy-2-thienylacetamido)-3-[1-(2-sulfoethyl)-tetrazol-5-ylthiomethyl]-3-cephem-4-carboxylic acid
7-(α-carboxy-2-thienylacetamido)-3-[1-(2-sulfamoylethyl)tetrazol-5-ylthiomethyl]-3-cephem-4-carboxylic acid
7-(α-carboxy-2-thienylacetamido)-3-[1-(2-sulfoethyl)-tetrazol-5-ylthiomethyl]-3-cephem-4-carboxylic acid
7-(α-sulfophenylacetamido)-3-[1-(2-sulfamoylethyl)tetrazol-5-ylthiomethyl]-3-cephem-4-carboxylic acid
7-(α-sulfophenylacetaido)-3-[1-(2-sulfoethyl)tetrazol-5-ylthiomethyl]-3-cephem-4-carboxylic acid.

EXAMPLE 25

When the N-t-butoxycarbonyl derivative of 7-(α-amino-2-thienylacetamido)cephalosporanic acid is reacted with 1-(2-sulfamoylethyl)tetrazole-5-thiol or 1-(2-sulfoethyl)tetrazole-5-thiol followed by removal of the protective groups as described above, 7-(α-amino-2-thienylacetamido)-3-[1-(2-sulfamoylethyl)tetrazol-5-ylthiomethyl]-3-cephem-4-carboxylic acid and 7-(α-amino-2-thienylacetamido)-3-[1-(2-sulfoethyl)tetrazol-5-ylthiomethyl]-3-cephem-4-carboxylic acid are obtained, respectively.

EXAMPLE 26

A mixture of 2.5 g. (7.7 mmol.) of D-α-(N-t-butoxycarbonyl)-4-aminophenylglycine, 1.8 g. (9.2 mmol.) of α-bromoacetic acid t-butyl ester and 2.5 g. (19.2 mmol.) of N,N-disopropylethylamine in 15 ml. of ethanol was stirred at 25° for 48 hours. The solvent was removed in vacuo, the residue was diluted with ethyl acetate and sodium bicarbonate and the pH was adjusted to 2.5. The layers were separated and the aqueous phase was again extracted with ethyl acetate. The combined extracts were washed with saturated sodium chloride solution, dried (MgSO$_4$) and evaporated to dryness to give D-α-(N-t-butoxycarbonyl)-4-t-butoxycarbonylmethylaminophenylglycine.

A solution of 0.380 g. (1.0 mmol.) of D-α-(N-t-butoxycarbonyl)-4-t-butoxycarbonylmethylaminophenylglycine, 0.296 g. (1.0 mmol.) of 7-aminocephalosporanic acid t-butyl ester and 0.210 g. (1.0 mmol.) of dicyclohexylcarbodiimide in 25 ml. of 9:1 ethyl acetate-methylene chloride was stirred at 0° for one hour. The reaction mixture was filtered and the filtrate was washed with 2.5% sulfuric acid, 5% sodium bicarbonate and water, dried (MgSO$_4$) and evaporated to dryness to give 7-(D-α-t-butoxycarbonylamino-4-carboxymethylaminophenylacetamido)cephalosporanic acid t-butyl ester. Deblocking was accomplished by stirring a mixture of the cephalosporanic acid t-butyl ester and 2 ml. of benzenethiol in 10 ml. of trifluoroacetic acid at 25° for one hour. Evaporation of the reaction mixture to dryness gave 7-(D-α-amino-4-carboxymethylaminophenylacetamido)cephalosporanic acid.

Reaction of the N-t-butoxycarbonyl derivative of 7-(D-α-amino-4-carboxymethylaminophenylacetamido)cephalosporanic acid with 1-(2-sulfamoylethyl)tetrazole-5-thiol or 1-(2-sulfoethyl)tetrazole-5-thiol according to procedures described hereinabove with subsequent removal of the protective group also as described above gives 7-(D-α-amino-4-carboxymethylaminophenylacetamido)-3-[1-(2-sulfamoylethyl)tetrazol-5-ylthiomethyl]-3-cephem-4-carboxylic acid and 7-(D-α-amino-4-carboxymethylaminophenylacetamido)-3-[1-(2-sulfoethyl)tetrazol-5-ylthiomethyl]-3-cephem-4-carboxylic acid, respectively.

EXAMPLE 27

When ethylamine or propylamine is used in the reaction with 2-phthalimidoethanesulfonyl chloride described in the procedure of Example 3 and the product formed is subjected to the synthetic steps described therein, the following tetrazole thiols are prepared:
1-(2-N-ethylsulfamoylethyl)tetrazole-5-thiol
1-(2-N-propylsulfamoylethyl)tetrazole-5-thiol.

Reaction of a tetrazole thiol listed above with 7-aminocephalosporanic acid, 7-D-mandelamidocephalosporanic acid, 7-(D-α-t-butoxycarbonylamino-4-hydroxyphenylacetamido)cephalosporanic acid, 7-(2-thienylacetamido)cephalosporanic acid and 7-trifluoromethylthioacetamidocephalosporanic acid, respectively, with removal of the protective groups when necessary, as described above, gives the following compounds of this invention:
7-amino-3-[1-(2-N-ethylsulfamoylethyl)tetrazol-5-ylthiomethyl]-3-cephem-4-carboxylic acid
7-amino-3-[1-(2-N-propylsulfamoylethyl)tetrazol-5-ylthiomethyl]-3-cephem-4-carboxylic acid
7-D-mandelamido-3-[1-(2-N-ethylsulfamoylethyl)tetrazol-5-ylthiomethyl]-3-cephem-4-carboxylic acid
7-D-mandelamido-3-[1-(2-N-propylsulfamoylethyl)tetrazol-5-ylthiomethyl]-3-cephem-4-carboxylic acid
7-(D-α-amino-4-hydroxyphenylacetamido)-3-[1-(2-N-ethylsulfamoylethyl)tetrazol-5-ylthiomethyl]-3-cephem-4-carboxylic acid
7-(D-α-amino-4-hydroxyphenylacetamido)-3-[1-(2-N-propylsulfamoylethyl)tetrazol-5-ylthiomethyl]-3-cephem-4-carboxylic acid
7-(2-thienylacetamido)-3-[1-(2-N-ethylsulfamoylethyl)tetrazol-5-ylthiomethyl]-3-cephem-4-carboxylic acid
7-(2-thienylacetamido)-3-[1-(2-N-propylsulfamoylethyl)tetrazol-5-ylthiomethyl]-3-cephem-4-carboxylic acid
7-trifluoromethylthioacetamido-3-[1-(2-N-ethylsulfamoylethyl)tetrazol-5-ylthiomethyl]-3-cephem-4-carboxylic acid
7-trifluoromethylthioacetamido-3-[1-(2-N-propylsulfamoylethyl)tetrazol-5-ylthiomethyl]-3-cephem-4-carboxylic acid

EXAMPLE 28

When diethylamine, dipropylamine or dibutylamine is substituted for dimethylamine in the procedure of Example 9, the following tetrazole thiols are prepared:
1-(2-N,N-diethylsulfamoylethyl)tetrazole-5-thiol
1-(2-N,N-dipropylsulfamoylethyl)tetrazole-5-thiol
1-(2-N,N-dibutylsulfamoylethyl)tetrazole-5-thiol.

Reaction of a tetrazole thiol listed above with 7-aminocephalosporanic acid, 7-D-mandelamidocephalosporanic acid, 7-(D-α-t-butoxycarbonylamino-4-hydroxyphenylacetamido)cephalosporanic acid, 7-(2-thienylacetamido)cephalosporanic acid and 7-trifluoromethylthioacetamidocephalosporanic acid, respectively, with removal of the protective groups when necessary, as described above, gives the following compounds of this invention:
7-amino-3-[1-(2-N,N-diethylsulfamoylethyl)tetrazol-5-ylthiomethyl]-3-cephem-4-carboxylic acid
7-amino-3-[1-(2-N,N-dipropylsulfamoylethyl)tetrazol-5-ylthiomethyl]-3-cephem-4-carboxylic acid
7-amino-3-[1-(2-N,N-dibutylsulfamoylethyl)tetrazol-5-ylthiomethyl]-3-cephem-4-carboxylic acid
7-D-mandelamido-3-[1-(2-N,N-diethylsulfamoylethyl)tetrazol-5-ylthiomethyl]-3-cephem-4-carboxylic acid
7-D-mandelamido-3-[1-(2-N,N-dipropylsulfamoylethyl)tetrazol-5-ylthiomethyl]-3-cephem-4-carboxylic acid
7-D-mandelamido-3-[1-(2-N,N-dibutylsulfamoylethyl)tetrazol-5-ylthiomethyl]-3-cephem-4-carboxylic acid
7-(D-α-amino-4-hydroxyphenylacetamido)-3-[1-(2-N,N-diethylsulfamoylethyl)tetrazol-5-ylthiomethyl]-3-cephem-4-carboxylic acid
7-(D-α-amino-4-hydroxyphenylacetamido)-3-[1-(2-N,N-dipropylsulfamoylethyl)tetrazol-5-ylthiomethyl]-3-cephem-4-carboxylic acid
7-(D-α-amino-4-hydroxyphenylacetamido)-3-[1-(2-N,N-dibutylsulfamoylethyl)tetrazol-5-ylthiomethyl]-3-cephem-4-carboxylic acid
7-(2-thienylacetamido)-3-[1-(2-N,N-diethylsulfamoylethyl)tetrazol-5-ylthiomethyl]-3-cephem-4-carboxylic acid
7-(2-thienylacetamido)-3-[1-(2-N,N-dipropylsulfamoylethyl)tetrazol-5-ylthiomethyl]-3-cephem-4-carboxylic acid
7-(2-thienylacetamido)-3-[1-(2-N,N-dibutylsulfamoylethyl)tetrazol-5-ylthiomethyl]-3-cephem-4-carboxylic acid
7-trifluoromethylthioacetamido-3-[1-(2-N,N-diethylsulfamoylethyl)tetrazol-5-ylthiomethyl]-3-cephem-4-carboxylic acid
7-trifluoromethylthioacetamido-3-[1-(2-N,N-dipropylsulfamoylethyl)tetrazol-5-ylthiomethyl]-3-cephem-4-carboxylic acid
7-trifluoromethylthioacetamido-3-[1-(2-N,N-dibutylsulfamoylethyl)tetrazol-5-ylthiomethyl]-3-cephem-4-carboxylic acid.

EXAMPLE 29

When a cephalosporanic acid listed below:
7-(1-tetrazolylacetamido)cephalosporanic acid
7-(3-sydnoneacetamido)cephalosporanic acid
7-(2-aminomethylphenylacetamido)cephalosporanic acid
is reacted with 1-(2-sulfamoylethyl)tetrazole-5-thiol by the procedure described in Example 3, the following compounds of this invention are obtained, respectively:
7-(1-tetrazolylacetamido)-3-[1-(2-sulfamoylethyl)tetrazol-5-ylthiomethyl]-3-cephem-4-carboxylic acid
7-(3-sydnoneacetamido)-3-[1-(2-sulfamoylethyl)tetrazol-5-ylthiomethyl]-3-cephem-4-carboxylic acid
7-(2-aminomethylphenylacetamido)-3-[1-(2-sulfamoylethyl)tetrazol-5-ylthiomethyl]-3-cephem-4-carboxylic acid.

Similarly, reaction of the sodium salt of a cephalosporanic acid listed above with 1-(2-sulfoethyl)tetrazole-5-thiol as described in Example 7 gives the following compounds of this invention:
7-(1-tetrazolylacetamido)-3-[1-(2-sulfoethyl)tetrazol-5-ylthiomethyl]-3-cephem-4-carboxylic acid
7-(3-sydnoneacetamido)-3-[1-(2-sulfoethyl)tetrazol-5-ylthiomethyl]-3-cephem-4-carboxylic acid
7-(2-aminomethylphenylacetamido)-3-[1-(2-sulfoethyl)tetrazol-5-ylthiomethyl]-3-cephem-4-carboxylic acid.

EXAMPLE 30

Reaction of the sodium salt of a cephalosporanic acid listed below:
7-(2,2,2-trifluoroethylthioacetamido)cephalosporanic acid
7-methylthioacetamidocephalosporanic acid
7-n-propylthioacetamidocephalosporanic acid
with 1-sulfomethyltetrazole-5-thiol sodium salt as described in the procedure of Example 14 gives the following compounds of this invention as final products:
7-(2,2,2-trifluoroethylthioacetamido)-3-(1-sulfomethyltetrazol-5-ylthiomethyl)-3-cephem-4-carboxylic acid
7-methylthioacetamido-3-(1-sulfomethyltetrazol-5-ylthiomethyl)-3-cephem-4-carboxylic acid
7-n-propylthioacetamido-3-(1-sulfomethyltetrazol-5-ylthiomethyl)-3-cephem-4-carboxylic acid.

EXAMPLE 31

Reaction of the sodium salt of a cephalosporanic acid listed in Example 30 with 1-(2-sulfamoylethyl)tetrazole-5-thiol sodium salt by the procedure of Example 14 gives the 7-substituted-3-[1-(2-sulfamoylethyl)tetrazol- 5-ylthiomethyl]-3-cephem-4-carboxylic acids listed below:

7-(2,2,2-trifluoroethylthioacetamido)-3-[1-(2-sulfamoylethyl)tetrazol-5-ylthiomethyl]-3-cephem-4-carboxylic acid $C_{15}H_{17}F_3N_7O_6S_4 \cdot Na \cdot 0.5\ CH_4O$: Calculated: 30.24% C; 3.11% H; 15.92% N; Found: 30.62% C; 3.00% H; 15.32% N.

7-methylthioacetamido-3-[1-(2-sulfamoylethyl)tetrazol-5-ylthiomethyl]-3-cephem-4-carboxylic acid 7-n-propylthioacetamido-3-[1-(2-sulfamoylethyl)tetrazol-5-ylthiomethyl]-3-cephem-4-carboxylic acid.

EXAMPLE 32

7-(2,2,2-Trifluoroethylsulfinylacetamido)-3-[1-(2-sulfamoylethyl)tetrazol-5-ylthiomethyl]-3-cephem-4-carboxylic acid To a stirred solution of 5.7 g. (0.03 mol.) of 2,2,2-trifluoroethylsulfinylacetic acid and 3.45 g. (0.03 mol.) of N-hydroxysuccinimide in 50 ml. of tetrahydrofuran at 0° is added 6.2 g. (0.031 mol.) of dicyclohexylcarbodiimide. The reaction mixture is stirred at 0° for one hour then at 25° for 12 hours. The precipitate is filtered and washed with tetrahydrofuran and the filtrate is evaporated to dryness to give the activated ester of 2,2,2-trifluoroethylsulfinylacetic acid.

A suspension of 4.17 g. (0.01 mol.) of 7-amino-3-[1-(2-sulfamoylethyl)tetrazol-5-ylthiomethyl]-3-cephem-4-carboxylic acid in 50 ml. of dry dimethylformamide is treated with 2 ml. of triethylamine and the mixture is stirred for 15 minutes at 25°. A slight excess of 0.01 mol. of the activated ester of 2,2,2-trifluoroethylsulfinylacetic acid is added to the mixture and it is stirred an additional hour. The reaction mixture is evaporated to dryness and water and ethyl acetate are added to the residue. The layers are separated, ethyl acetate is added to the aqueous phase and it is acidified to pH 2.5 by addition of 6 N hydrochloric acid. The mixture is filtered, the layers are separated and the aqueous phase is extracted with ethyl acetate. The extract is washed with water, dried (MgSO₄) and evaporated to dryness to give the title compound.

EXAMPLE 33

7-(2,2,2-Trifluoroethylsulfonylacetamido)-3-[1-(2-sulfamoylethyl)tetrazol-5-ylthiomethyl]-3-cephem-4-carboxylic acid To a solution of 9.0 g. (0.019 mol.) of 7-amino-3-[1-(2-sulfamoylethyl)tetrazol-5-ylthiomethyl]-3-cephem-4-carboxylic acid t-butyl ester and 3.9 g. (0.019 mol.) of 2,2,2-trifluoroethylsulfonylacetic acid in tetrahydrofuran is added dropwise a solution of 3.9 g. (0.019 mol.) of dicyclohexylcarbodiimide in 100 ml. of tetrahydrofuran. The reaction mixture is stirred at 25° for 12 hours, then filtered and concentrated to about 10 ml. The residue is filtered and evaporated to dryness to give 7-(2,2,2-trifluoroethylsulfonylacetamido)-3-[1-(2-sulfamoylethyl)tetrazol-5-ylthiomethyl]-3-cephem-4-carboxylic acid t-butyl ester.

The ester is dissolved in acetonitrile and trifluoroacetic acid is added. The solution is stirred for three hours, then evaporated to dryness to give the title compound.

EXAMPLE 34

7-Methylthioacetamido-3-[1-(2-sulfamoylethyl)tetrazol-5-ylthiomethyl]-3-cephem-4-carboxylic acid To a stirred, cooled (−20°) solution of 10.8 g. (0.026 mol.) of 7-amino-3-[1-(2-sulfamoylethyl)tetrazol-5-ylthiomethyl]-3-cephem-4-carboxylic acid in 220 ml. of 3% sodium bicarbonate and 220 ml. of acetone is dropwise added a solution of 3.66 g. (0.029 mol.) of methylthioacetyl chloride in 52 ml. of acetone, during which time the pH of the reaction mixture is maintained at 8.0 by addition of 10% sodium hydroxide. After addition the reaction mixture is stirred an additional 20 minutes at −15°, then is warmed to 25° and extracted with ether. The remaining aqueous phase is cooled, 250 ml. of ethyl acetate is added and the slurry is acidified with 3 N hydrochloric acid. The layers are separated and the aqueous phase is extracted twice more with ethyl acetate. The combined extracts are dried (MgSO₄) and evaporated to dryness to yield the title compound.

EXAMPLE 35

7-n-Propylthioacetamido-3-[1-(2-sulfamoylethyl)tetrazol-5-ylthiomethyl]-3-cephem-4-carboxylic acid The title compound is prepared by substitution of n-propylthioacetyl chloride in the procedure of Example 34 for methylthioacetyl chloride.

EXAMPLE 36

7-(α-Carboxy-2-thienylacetamido)-3-(1-sulfomethyltetrazol-5-ylthiomethyl)-3-cephem-4-carboxylic acid 7-Aminocephalosporanic acid (0.73 g., 2.68 mmol.) is suspended in 10 ml. of dry dimethylformamide and 1.12 ml. of triethylamine is added. A solution of 0.91 g. (2.68 mmol.) of the activated ester of α-t-butoxycarbonyl-2-thienylacetamide, prepared as described above, in 2 ml. of dimethylformamide is added and the reaction mixture is stirred at 25° for three hours. An additional 0.45 g. of activated ester is then added and the mixture is stirred another five hours. Ether (ca. 300 ml.) is added and the solution is decanted. The remaining material is washed with ether, dissolved in water and the aqueous solution is extracted with ethyl acetate. The pH of the ethyl acetate solution is adjusted to 1.5 by addition of dilute hydrochloric acid. Extraction with ethyl acetate and evaporation of the solvent gives 7-(α-t-butoxycarbonyl-2-thienylacetamido)cephalosporanic acid.

A solution of 11.8 g. (0.06 mol.) of 1-sulfomethyltetrazole-5-thiol in 120 ml. of water is added to a warm (45°) solution of 19.9 g. (0.04 mol.) of 7-(α-t-butoxycarbonyl-2-thienylacetamido)cephalosporanic acid in a mixture of 220 ml. of water and 8.4 g. (0.01 mol.) of sodium bicarbonate. The temperature is raised to 65° and the pH maintained at 7.4–7.6 by addition of aqueous sodium carbonate solution. After three hours, the reaction mixture is cooled to 10° and adjusted to pH 3.5 by addition of dilute hydrochloric acid. The pH is adjusted to 7.0 by addition of base and the aqueous solution is passed through a XAD-4 resin column eluting with water and methanol to give the title compound as its disodium salt.

7-(α-t-Butoxycarbonyl-2-thienylacetamido)-3-(1-sulfomethyltetrazol-5-ylthiomethyl)-3-cephem-4-carboxylic acid disodium salt (1.0 g.) is stirred in a mixture of 10 ml. of trifluoroacetic acid and 10 ml. of m-dimethoxybenzene at 25° for one hour. The mixture is evaporated to dryness and the residue is triturated with ether. The precipitated product is collected by filtration and dissolved in methanol. A sodium methoxide solution is added until pH 7.0, the mixture is diluted with ether and the product is dissolved in water and lyophilized to give 7-(α-carboxy-2-thienylacetamido)-3-(1-sulfomethyltetrazol-5-ylthiomethyl)-3-cephem-4-carboxylic acid trisodium salt.

The trisodium salt is converted to the title compound by treating the salt with IR-120H ion exchange resin as previously described.

EXAMPLE 37

7-(2-Thienylacetamido)-3-(1-sulfomethyltetrazol-5-ylthiomethyl)-3-cephem-4-carboxylic acid Reaction of 2.18 g. (0.01 mol.) of 1-sulfomethyltetrazol-5-thiol sodium salt, 5.23 g. (0.012 mol.) of 7-(2-thienylacetamido)cephalosporanic acid sodium salt and 0.84 g. (0.01 mol.) of sodium bicarbonate as described in the procedure of Example 14 gave the title compound as the corresponding disodium salt.

$C_{16}H_{14}N_6O_7S_4.2$ Na.0.75 $C_2H_6O$: Calculated: 34.81% C; 3.09% H; 13.56% N; Found: 34.41% C; 3.03% H; 13.76% N.

7-(2-Thienylacetamido)-3-(1-sulfomethyltetrazol-5-ylthiomethyl)-3-cephem-4-carboxylic acid disodium salt is converted to the title compound as described above.

EXAMPLE 38

7-(2-Thienylacetamido)-3-[1-(2-sulfoethyl)tetrazol-5-ylthiomethyl]-3-cephem-4-carboxylic acid Reaction of 5.68 g. (0.01 mol.) of 1-(2-sulfoethyl)tetrazole-5-thiol cyclohexylamine salt and 5.23 g. (0.0125 mol.) of 7-(2-thienylacetamido)cephalosporanic acid sodium salt in 80 ml. of water containing sufficient sodium bicarbonate to maintain the pH at 7.0, as described in the procedure of Example 14, gave the title compound.

EXAMPLE 39

7-Trifluoromethylthioacetamido-3-[1-(3-sulfamoylpropyl)tetrazol-5-ylthiomethyl]-3-cephem-4-carboxylic acid Reaction of 1-(3-sulfamoylpropyl)tetrazole-5-thiol sodium salt, prepared as previously described, and 7-trifluoromethylthioacetamidocephalosporanic acid sodium salt according to the procedure described in Example 14 gives the title compound as its sodium salt.

7-Trifluoromethylthioacetamido-3-[1-(3-sulfamoylpropyl)tetrazol-5-ylthiomethyl]-3-cephem-4-carboxylic acid sodium salt is converted to the title compound as described in Example 14.

EXAMPLE 40

7-Amino-3-(1-sulfomethyltetrazol-5-ylthiomethyl)-3-cephem-4-carboxylic acid

To a mixture of 97 g. (200 ml., 2.1 mol.) of formic acid, distilled from anhydrous copper sulfate, and 37.5 ml. (0.4 mol.) of acetic anhydride was added 25.0 g. (0.1 mol.) of 7-aminocephalosporanic acid. The mixture was stirred at ambient temperature for 0.5 hour, then evaporated to dryness. The residue was dissolved in ethyl acetate and the ethyl acetate solution was filtered and evaporated to dryness to give a residue which was recrystallized from ether-petroleum ether to give 7-formamidocephalosporanic acid.

A mixture of 1.0 g. (3.3 mmol.) of 7-formamidocephalosporanic acid and 0.7 g. (2.6 mmol.) of 1-sulfomethyltetrazole-5-thiol disodium salt in 15 ml. of water was stirred at 65°–70° for 3 hours while maintaining the pH at 7.0 by addition of sodium bicarbonate and/or hydrochloric acid. The mixture was cooled, acidified to pH 1.0 with hydrochloric acid and extracted with ethyl acetate. The extract was filtered and the filtrate was evaporated to dryness to give a residue which was dissolved in 30 ml. of methanol. The methanol solution was filtered, 30–40 ml. of isopropanol and ethanol were added, the solution was filtered again and 100 ml. of ether was added. The precipitate was collected by filtration and dried to give the title compound.

$C_{10}H_{12}O_6N_6S_3.0.33$ $C_3H_8O.HCl.2$ $H_2O$: Calculated: 27.0% C; 3.50% H; 16.95% N; Found: 26.96% C; 3.23% H; 16.53% N.

EXAMPLE 41

7-(4-Pyridylthioacetamido)-3-(1-sulfomethyltetrazol-5-ylthiomethyl)-3-cephem-4-carboxylic acid (4-Pyridylthio)acetyl chloride (0.53 g., 2.8 mmol.) was dropwise added to a mixture of 1.0 g. of 7-amino-3-(1-sulfomethyltetrazol-5-ylthiomethyl)-3-cephem-4-carboxylic acid (mixture of sodium salt, free acid and sodium chloride) and 0.9 g. (9.0 mmol.) of triethylamine in 10 ml. of dry dimethylformamide. The reaction mixture was stirred for 1.5 hour at −10°, then it was warmed to ambient temperature and stirred for 1 hour. The mixture was filtered and the filtrate was diluted with 200 ml. of ether-petroleum ether. The precipitate was collected by filtration and dissolved in warm methanol. The methanol solution was filtered and the filtrate was concentrated to 10 ml. Ethanol (50 ml.) was added and the precipitate was collected by filtration and washed with ether to give the title compound as the sodium salt. Additional amounts of the salt were obtained by addition of ether to the filtrate.

$C_{17}H_{16}N_7O_7S_4.Na.NaCl.C_6H_{15}N$: Calculated: 37.23% C; 4.21% H; 15.10% N; Found: 36.84% C; 4.48% H; 15.43% N.

7-(4-Pyridylthioacetamido)-3-(1-sulfomethyltetrazol-5-ylthiomethyl)-3-cephem-4-carboxylic acid sodium salt is converted to the title compound by procedures described above.

EXAMPLE 42

Acylation of 7-amino-3-(1-sulfomethyltetrazol-5-ylthiomethyl)-3-cephem-4-carboxylic acid with an activated derivative of the following acids:
cyanoacetic acid
3-pyridylthioacetic acid
cyanomethylthioacetic acid
2,2,2-trifluoroethylsulfinylacetic acid
trifluoromethylsulfonylacetic acid
as described in the procedure of Example 41 gives the following compounds of this invention:
7-cyanoacetamido-3-(1-sulfomethyltetrazol-5-ylthiomethyl)-3-cephem-4-carboxylic acid
7-(3-pyridylthioacetamido)-3-(1-sulfomethyltetrazol-5-ylthiomethyl)-3-cephem-4-carboxylic acid
7-cyanomethylthioacetamido-3-(1-sulfomethyltetrazol-5-ylthiomethyl)-3-cephem-4-carboxylic acid 7-(2,2,2-trifluoroethylsulfinylacetamido)-3-(1-sulfomethyltetrazol-5-ylthiomethyl)-3-cephem-4-carboxylic acid 7-trifluoromethylsulfonylacetamido-3-(1-sulfomethyltetrazol-5-ylthiomethyl)-3-cephem-4-carboxylic acid.

EXAMPLE 43

7-(D-α-Formyloxyphenylacetamido)-3-(1-sulfomethyltetrazol-5-ylthiomethyl)-3-cephem-4-carboxylic acid 7-Amino-3-(1-sulfomethyltetrazol-5-ylthiomethyl)-3-cephem-4-carboxylic acid is reacted with the formate ester of D-mandeloyl chloride according to the procedure of Example 41 to give the title compound.

EXAMPLE 44

7-(D-α-Formyloxyphenylacetamido)-3-[1-(2-sulfamoylethyl)tetrazol-5-ylthiomethyl]-3-cephem-4-carboxylic acid Substitution of an equivalent amount of 7-amino-3-[1-(2-sulfamoylethyl)tetrazol-5-ylthiomethyl]-3-cephem-4-carboxylic acid in the procedure of Example 43 for 7-amino-3-(1-sulfomethyltetrazol-5-ylthiomethyl)-3-cephem-4-carboxylic acid gives the title compound.

EXAMPLE 45

Using the procedures described above for the preparation of compounds of this invention, the following compounds were prepared:

7-(1-tetrazolylacetamido)-3-(1-sulfomethyltetrazol-5-ylthiomethyl)-3-cephem-4-carboxylic acid $C_{13}H_{12}N_{10}O_7S_3.2$ Na: Calculated: 27.76% C; 2.15% H; 24.90% N; Found: 27.55% C; 3.21% H; 23.00% N.

7-(3-sydnoneacetamido)-3-(1-sulfomethyltetrazol-5-ylthiomethyl)-3-cephem-4-carboxylic acid $C_{14}H_{10}N_8O_9S_3.2$ Na.3 $H_2O.2$ $CH_4O$: Calculated: 27.59% C; 3.72% H; 16.08% N; Found: 27.59% C; 3.02% H; 15.67% N.

7-trifluoromethylthioacetamido-3-[1-(4-sulfobutyl)tetrazol-5-ylthiomethyl]-3-cephem-4-carboxylic acid $C_{16}H_{17}F_3N_6O_7S_4.2$ Na.$H_2O$: Calculated: 29.36% C; 2.93% H; 12.84% N; Found: 29.31% C; 3.33% H; 12.76% N.

7-(2-thienylacetamido)-3-[1-(4-sulfobutyl)tetrazol-5-ylthiomethyl]-3-cephem-4-carboxylic acid $C_{19}H_{20}N_6O_7S_4.2$ Na.2 $H_2O.2$ $C_2H_6O$: Calculated: 34.85% C; 3.69% H; 12.83% N; 19.59% S; Found: 34.52% C; 3.88% H; 13.54% N; 19.09% S.

7-(2-thienylacetamido-3-[1-(5-sulfopentyl)tetrazol-5-ylthiomethyl]-3-cephem-4-carboxylic acid.

$C_{20}H_{22}N_6O_7S_4.2$ Na.2.5 $H_2O.1.75$ $C_2H_6O$: Calculated: 36.33% C; 4.77% H; 11.29% N; 17.23% S; Found: 36.46% C; 4.30% H; 11.63% N; 17.30% S.

EXAMPLE 46

7α-Methoxy-7β-(2-thienylacetamido)-3-(1-sulfomethyltetrazol-5-ylthiomethyl)-3-cephem-4-carboxylic acid A solution of 1.28 g. (3 mmol.) of 7α-methoxy-7β-(2-thienylacetamido)cephalosporanic acid sodium salt is dissolved in 50 ml. of water, 1.08 g. (4.5 mmol.) of 1-sulfomethyltetrazole-5-thiol disodium salt is added and the solution is heated at 70° until thin layer chromatography indicates consumption of the starting material (ca. 5 hours). The reaction mixture is chromatographed on XAD-4 ion exchange resin with, after washing with water, methanol as eluant. Evaporation of the methanol solution gives the title compound as the disodium salt.

7α-Methoxy-7β-(2-thienylacetamido)-3-(1-sulfomethyltetrazol-5-ylthiomethyl)-3-cephem-4-carboxylic acid disodium salt is converted to the title compound as described above.

EXAMPLE 47

7α-Methoxy-7β-trifluoromethylthioacetamido-3-(1-sulfomethyltetrazol-5-ylthiomethyl)-3-cephem-4-carboxylic acid To a cold solution of 5.25 g. (0.012 mol.) of 7β-amino-7α-methoxycephalosporanic acid benzhydryl ester in 200 ml. of methylene chloride containing 1.79 g. (0.012 mol.) of N,N-diethylaniline is added dropwise over a 20 minute period a solution of 1.82 g. (0.012 mol.) of trifluoromethylthioacetyl chloride in 50 ml. of methylene chloride. After stirring for 30 minutes, the mixture is extracted successively with 5% aqueous sodium bicarbonate, 5% aqueous hydrochloric acid and finally with brine. The organic phase is dried (MgSO$_4$) and the solvent evaporated to give 7α-methoxy-7β-trifluoromethylthioacetamidocephalosporanic acid benzhydryl ester.

7α-Methoxy-7β-trifluoromethylthioacetamidocephalosporanic acid benzhydryl ester is dissolved in a cold mixture of trifluoroacetic acid-anisole (2:1) and the mixture is stirred for 1.5 hr. without external cooling. The solvent is evaporated in vacuo and the residual product is taken up in ethyl acetate, washed with water, dried (MgSO$_4$) and concentrated in vacuo to a small volume. This solution is added dropwise to stirred petroleum ether to yield 7α-methoxy-7β-trifluoromethylthioacetamidocephalosporanic acid.

7α-Methoxy-7β-trifluoromethylthioacetamidocephalosporanic acid (2.2 g., 5 mmol.), is suspended in 75 ml. of water and 0.4 g. of solid sodium bicarbonate is added until solution is complete. To this solution is added 1.8 g. (7.5 mmol.) of 1-sulfomethyltetrazole-5-thiol disodium salt and the mixture is heated at 70° for 7 hours. The pH of the reaction mixture is maintained at 7.5 by dropwise addition of 3 N hydrochloric acid as necessary. Progress of the reaction is monitored by thin layer chromatography and judged to be complete when tlc indicates disappearance of starting material. The reaction mixture is chromatographed on a column of XAD-4 resin and the product is eluted from the column with methanol. Evaporation of the methanol solution gives 7α-methoxy-7β-trifluoromethylthioacetamido-3-(1-sulfomethyltetrazol-5-ylthiomethyl)-3-cephem-4-carboxylic acid disodium salt.

The disodium salt is converted to the title compound by procedures described hereinabove.

EXAMPLE 48

7β-D-Mandelamido-7α-methoxy-3-(1-sulfomethyltetrazol-5-yl-thiomethyl)-3-cephem-4-carboxylic acid A cold solution of 2.6 g. (6 mmol.) of 7β-amino-7α-methoxycephalosporanic acid benzhydryl ester in 100 ml. of methylene chloride containing 0.9 g. (6 mmol.) of N,N-diethylaniline is treated dropwise over a 15 minute period with a solution of 1.7 g. (6 mmol.) of D-O-dichloroacetylmandeloyl chloride in 25 ml. of methylene chloride. The reaction mixture is allowed to come to room temperature with stirring and then is extracted successively with 5% aqueous sodium bicarbonate, 5% hydrochloric acid and brine. The organic phase is dried and evaporated in vacuo. The residue is dissolved in cold trifluoroacetic acid-anisole (2:1) and the mixture is stirred at ambient temperature for 1 hour. The mixture is evaporated in vacuo and the residue is dissolved in 5% aqueous sodium bicarbonate. The pH is raised to 9–9.3 by addition of 5% aqueous sodium carbonate and maintained there for 30 minutes to complete cleavage of the dichloroacetyl group. The solution is cooled in ice, layered with ethyl acetate and acidified to pH 2.0 with dilute hydrochloric acid. The layers are separated and after a second extraction of the aqueous layer with ethyl acetate the organic phases are combined, dried and evaporated in vacuo to yield 7β-D-mandelamido-7α-methoxycephalosporanic acid.

7β-D-mandelamido-7α-methoxycephalosporanic acid (2.2 g., 5 mmol.) is suspended in 75 ml. of water and solid sodium bicarbonate is added until all of the acid has dissolved. To this is added 1.8 g. (7.5 mmol.) of 1-sulfomethyltetrazole-5-thiol disodium salt and the mixture is heated at 70° for 7 hours. The pH of the reaction mixture is maintained at 7.5 by addition of 3 N hydrochloric acid. Chromatography of this solution on XAD-4 resin while eluting with methanol gives, upon evaporation of the methanol, the title compound as its disodium salt.

7β-D-Mandelamido-7α-methoxy-3-(1-sulfomethyl-tetrazol-5-ylthiomethyl)-3-cephem-4-carboxylic acid disodium salt is converted to the title compound by procedures described hereinabove.

EXAMPLE 49

7α-Methoxy-7β-(D-α-aminophenylacetamido)-3-[1-(2-sulfoethyl)tetrazol-5-ylthiomethyl]-3-cephem-4-carboxylic acid To a solution of 5.3 g. (0.012 mol.) of 7β-amino-7α-methoxycephalosporanic acid p-nitrobenzyl ester in 200 ml. of methylene chloride is added 3.0 g. (0.012 mol.) of D-α-t-butoxycarbonylaminophenylacetic acid and 2.5 g. (0.012 mol.) of dicyclohexylcarbodiimide. The mixture is stirred for 18 hours at ambient temperature then filtered. The filtrate is evaporated in vacuo and the residue is dissolved in methanoltetrahydrofuran and hydrogenated over 5% palladium on carbon to give 7β-(D-α-t-butoxycarbonylaminophenylacetamido)-7α-methoxycephalosporanic acid.

7β-(D-α-t-Butoxycarbonylaminophenylacetamido)-7α-methoxycephalosporanic acid (2.68 g., 5 mmol.) is dissolved in 75 ml. of water by adding 0.4 g. of solid sodium bicarbonate. 1-(2-Sulfoethyl)tetrazole-5-thiol disodium salt (1.9 g., 7.5 mmol.) is added and the reaction mixture is heated at 70° until thin layer chromatography indicates that the starting material has disappeared. The reaction mixture is chromatographed on XAD-4 resin and eluted with methanol. Evaporation of the methanol solution gives 7α-methoxy-7β-(D-α-t-butoxycarbonylaminophenylacetamido)-3-[1-(2-sulfoethyl)tetrazol-5-ylthiomethyl]-3-cephem-4-carboxylic acid disodium salt.

The disodium salt is suspended in 1:1 trifluoroacetic acid-anisole and stirred at ambient temperature for two hours. Excess trifluoroacetic acid is removed by evaporation, the residue is triturated with ether and the resulting precipitate is collected by filtration and stirred with acetonitrile to give the title compound as its trifluoroacetic acid salt.

An aqueous solution of the trifluoroacetic acid salt is brought to pH 7 by addition of 5% aqueous sodium bicarbonate then chromatographed on XAD-4 resin with methanol as eluant. The solid material obtained after evaporation of the methanol is dissolved in water and the aqueous solution is passed through a cation exchange column (IR-120H). Lyophilization of the eluted material gives the title compound.

EXAMPLE 50

7β-D-Mandelamido-7α-methoxy-3-[1-(2-sulfamoylethyl)tetrazol-5-ylthiomethyl]-3-cephem-4-carboxylic acid To a suspension of 21.1 g. (0.05 mol.) of 7-amino-3-[1-(2-sulfamoylethyl)tetrazol-5-ylthiomethyl]-3-cephem-4-carboxylic acid in 500 ml. of dry methylene chloride is added in one portion a solution of 30.0 g. (0.15 mol.) of O-t-butyldiisopropylpseudourea in 50 ml. of methylene chloride. The mixture is stirred at ambient temperature for 24 hours. The precipitate is removed by filtration and the filtrate evaporated to a residue which is taken up in 200 ml. of benzene and filtered again. The filtrate is extracted with three 100 ml. portions of cold 1 N hydrochloric acid. The acidic aqueous extracts are layered with ethyl acetate and the pH adjusted to 7.5 with solid sodium bicarbonate. The organic layer is separated and the aqueous phase is extracted with two 150 ml. portions of ethyl acetate. The combined extracts are dried (MgSO$_4$), filtered and evaporated to give 7-amino-3-[1-(2-sulfamoylethyl)tetrazol-5-ylthiomethyl]-3-cephem-4-carboxylic acid t-butyl ester.

A solution of 1.91 g. (4 mmol.) of 7-amino-3-[1-(2-sulfamoylethyl)tetrazol-5-ylthiomethyl]-3-cephem-4-carboxylic acid t-butyl ester and 0.94 g. (4 mmol.) of 3,5-di-t-butyl-4-hydroxybenzaldehyde in 150 ml. of dry benzene is refluxed for ca. 4 hours under a Dean-Stark trap until no more water separates. The solution is evaporated under reduced pressure to give a residue which is dissolved in 150 ml. of 1,2-dichloroethane and cooled to 0°–5° in an ice bath. Freshly prepared lead dioxide (5 g.) is added in 1 g. portions over 30 minutes and the reaction is stirred in the cold until complete consumption of the starting material is indicated by thin layer chromatography. The mixture is then filtered through Celite and the filter cake is washed with two 30 ml. portions of cold 1,2-dichloroethane. The filtrate is treated with 30 ml. of dry methanol (distilled from magnesium) and the reaction is stirred at ambient temperature for 3 hours until complete consumption of the intermediate and formation of a new product is shown by thin layer chromatography. The reaction mixture is evaporated to dryness and the residue is taken up in 50 ml. of methanol and treated with 4.0 g. of Girard reagent T (trimethylaminoacetohydrazide chloride). This solution is stirred at ambient temperature for 3 hours and evaporated under vacuum to give a solid residue which is partitioned between 150 ml. of ethyl acetate and 100 ml. of 20% aqueous sodium chloride solution. The organic phase is washed with three 100 ml. portions of 10% aqueous sodium chloride, two 100 ml. portions of water and 100 ml. of a saturated sodium chloride solution. The organic phase is dried (MgSO$_4$), filtered and evaporated to dryness to give 7β-amino-7α-methoxy-3-[1-(2-sulfamoylethyl)tetrazol-5-ylthiomethyl]-3-cephem-4-carboxylic acid t-butyl ester.

A solution of 0.95 g. (2 mmol.) of 7β-amino-7α-methoxy-3-[1-(2-sulfamoylethyl)tetrazol-5-ylthiomethyl]-3-cephem-4-carboxylic acid t-butyl ester and 0.30 g. (2 mmol.) of N,N-diethylaniline in 100 ml. of dry methylene chloride is stirred at 0°–5° while 0.56 g. (2 mmol.) of D-O-dichloroacetylmandeloyl chloride in 10 ml. of methylene chloride is added dropwise over a 10 minute period. The mixture is stirred in the cold for 30 minutes then warmed to room temperature and stirred for an additional 30 minutes. The solution is washed with 50 ml. of cold dilute hydrochloric acid and 50 ml. of cold 5% aqueous sodium bicarbonate, dried (MgSO$_4$) and evaporated to dryness. The residue is dissolved in a mixture of 10 ml. of trifluoroacetic acid and 2 ml. of m-dimethoxybenzene and stirred at ambient temperature for 2 hours. The excess trifluoroacetic acid is evaporated under vacuum and the residue is partitioned between 50 ml. of ether 50 ml. of water. The pH is adjusted to 9.3–9.5 with 5% aqueous sodium carbonate and the organic phase is separated and discarded. The aqueous phase is stirred at pH 9.3–9.5 for 30 minutes, extracted with 50 ml. of ethyl acetate which is discarded, layered with fresh ethyl acetate and adjusted to pH 1.5 with dilute hydrochloric acid. The aqueous layer is extracted with three 50 ml. portions of ethyl acetate and the combined extracts are dried and evaporated to a small volume. Petroleum ether is added dropwise to precipitate the title compound which is collected and dried.

EXAMPLE 51

7-(o-Aminomethylphenylacetamido)-3-(1-sulfomethyltetrazol-5-ylthiomethyl)-3-cephem-4-carboxylic acid A solution of o-(N-t-butoxycarbonylaminomethyl)phenylacetic acid (5.3 g, 20 mmol), triethylamine (2.77 ml) and N-methylmorpholine (4 drops) in tetrahydrofuran (150 ml) was cooled to −10° and treated with i-butyl chloroformate (2.72 g, 20 mmol). The resulting solution was stirred for 10 minutes and then an ice cold solution of 7-ACA (5.44 g, 20 mmol) and triethylamine (2.77 ml) in 1:1 tetrahydrofuran water (100 ml) was added at a rate so that the temperature remained at −10°. The reaction was stirred for 3 hours without cooling, the organic solvents were removed by distillation and water (100 ml) was added. The solution was adjusted to pH 7.5 with triethylamine and extracted with ethyl acetate. The aqueous phase was layered with ethyl acetate, adjusted to pH 2.3 with 3 N HCl and the phases were separated. The aqueous phase was re-extracted with fresh ethyl acetate and the combined extracts were dried. Removal of the solvent in vacuo left an oil; 6.0 g.

To a solution of NaHCO$_3$ (0.49 g) in water (75 ml) was added the above product (3.0 g, 5.8 mmol). When solution was complete, 1-sulfomethyltetrazole-5-thiol disodium salt was added. The solution was stirred and heated at 60° while maintaining a pH of 7.0 to 7.2 by adding 5% NaHCO$_3$ as needed.

After 4.75 hours the reaction was cooled to room temperature and extracted with ethyl acetate. The aqueous solution was adjusted to pH 7.0 and then applied to a column of "Amberlite XAD-7" resin (2"×34") which had been pre-washed with methanol followed by water. The product was eluted from the column with water at a flow rate of 10 ml per minute. The fractions containing the product were freeze dried to yield 1.6 g of t-BOC protected product.

To an ice cold mixture of trifluoroacetic fluid (20 ml) and dimethoxybenzene (20 ml) was added with stirring the above t-BOC protected product (1.6 g). Cooling was discontinued and the reaction was stirred for 20 minutes. The trifluoroacetic acid was removed in vacuo and the remaining liquid was stirred while fresh ether was added to precipitate the trifluoroacetate salt of the title compound. The product was collected, washed with ether, stirred vigorously with acetonitrile (100 ml) for 2 hours and then recollected and washed with fresh acetonitrile to give the salt of the title compound; 880 mg.

EXAMPLE 52

7β-(o-Aminomethylphenylacetamido)-7α-methoxy-3-(1-sulfomethyltetrazol-5-ylthiomethyl)-3-cephem-4-carboxylic acid Reacting 7β-(o-N-t-butoxycarbonylaminomethylphenylacetamido)-7α-methoxycephalosporanic acid and 1-sulfomethyltetrazole-5-thiol disodium salt and then deblocking with trifluoroacetic acid all according to the procedures in Example 51 gives the title product.

Alternatively, 7β-(o-N-t-butoxycarbonylaminomethylphenylacetamido)-7α-methoxycephalosporanic acid and 1-sulfomethyltetrazole 5-thiol disodium salt can be reacted together in 0.1 M phosphate buffer pH 7.0 at 85° until the reaction is completed to give (after treatment with trifluoroacetic acid) the title product.

EXAMPLE 53

Using procedures analogous to Example 52 the following compounds are prepared:
7β-(2-thienylacetamido)-7α-methoxy-3-(1-sulfomethyltetrazol-5-ylthiomethyl)-3-cephem-4-carboxylic acid
7β-(1-tetrazolylacetamido)-7α-methoxy-3-(1-sulfomethyltetrazol-5-ylthiomethyl)-3-cephem-4-carboxylic acid.
7β-(3-sydnoneacetamido)-7α-methoxy-3-(1-sulfomethyltetrazol-5-ylthiomethyl)-3-cephem-4-carboxylic acid
7β-(cyanoacetamido)-7α-methoxy-3-(1-sulfomethyltetrazol-5-ylthiomethyl)-3-cephem-4-carboxylic acid

EXAMPLE 54

7-(4-Aminomethylphenylacetamido)-3-(1-sulfomethyltetrazol-5-ylthiomethyl)-3-cephem-4-carboxylic acid A mixture of 7.76 g (38.5 mmol) of 4-aminomethylphenylacetic acid hydrochloride, 10.42 g (42.3 mmol) of 2-t-butoxycarbonyloxyimino-2-phenylacetonitrile and 13.33 ml (96.2 mmol) of triethylamine in 60 ml of 50% aqueous dioxane was stirred for 2.5 hours at ambient temperature. The solvent was removed, 25 ml of water and 50 ml of ethyl acetate were added and the layers were separated. The aqueous phase was extracted with ethyl acetate then stirred with ethyl acetate and acidified to pH 1–1.5 with 3 N hydrochloric acid. The mixture was then extracted three times with ethyl acetate and the combined extracts were washed with water, dried (MgSO$_4$) and evaporated to give 4-(N-t-butoxycarbonylaminomethyl)phenylacetic acid, m.p. 108°–110°.

Substitution of an equivalent amount of 4-(N-t-butoxycarbonylaminomethyl)phenylacetic acid in the procedure of Example 51 for 2-(N-t-butoxycarbonylaminomethyl)phenylacetic acid gave 7-(4-N-t-butoxycarbonylaminomethylphenylacetamido)cephalosporanic acid.

Reaction of 0.65 g (1.2 mmol) of 7-(4-N-t-butoxycarbonylaminomethylphenylacetamido)cephalosporanic acid, 0.34 g (10% excess) of 1-sulfomethyltetrazole-5-thiol disodium salt and 0.11 g (1.2 mmol) of sodium bicarbonate according to the procedure described in Example 51, followed by chromatography of the reaction mixture after adjustment to pH 7.2 on a XAD-7 resin column with distilled water as eluant ultimately gave 7-(4-N-t-butoxycarbonylaminomethylphenylacetamido)-3-(1-sulfomethyltetrazol-5-ylthiomethyl)-3-cephem-4-carboxylic acid disodium salt.

7-(4-N-t-butoxycarbonylaminomethylphenylacetamido)-3-(1-sulfomethyltetrazol-5-ylthiomethyl)-3-cephem-4-carboxylic acid disodium salt (0.35 g, 0.5 mmol) was stirred in an ice bath with a cold mixture of 5 ml of trifluoroacetic acid and 2.5 ml of anisole for 20 minutes, then without cooling for an additional 20 minutes. The trifluoroacetic acid was removed in vacuo and the residue was stirred one hour with ether. The solid was collected, washed with ether and dried ($P_2O_5$) to give the title compound as the trifluoroacetate salt.

$C_{21}H_{22}F_3N_7O_9S_3$. 0.5 $H_2O$. 0.5 $C_4H_{10}O$: Calculated: 37.44% C; 3.99% H; 13.79% N; Found: 37.00% C; 3.70% H; 12.82% N.

| In vitro activity: Bacteria | MIC (µg/ml) |
|---|---|
| Staph. aureus HH 127 | 6.3 (0.8)* |
| Staph. aureus 671 | 3.1 (0.8) |
| Staph. aureus 674 | 3.1 (0.4) |
| Strep. faecalis HH 34358 | 100 (25) |
| E. coli SK&F 12140 | 6.3 (0.8) |
| E. coli 804 | >100 (100) |
| Kleb. pneumoniae SK&F 4200 | 0.4 (3.1) |
| Kleb. pneumoniae SK&F 1200 | 0.4 (0.4) |
| Kleb. pneumoniae 982 | >100 (>100) |
| Pseudo. aeruginosa HH 63 | >100 (>100) |
| Pseudo. aeruginosa 647 | >100 (>100) |
| Serratia marcescens ATCC 13880 | >100 (>100) |
| Proteus morgani 179 | >100 (>100) |
| Proteus mirabilis 444 | 1.6 (3.1) |
| Enterobacter aerogenes 13048 | >100 (3.1) |
| Enterobacter cloacae 921 | 100 (25) |

*Cefazolin
In vivo activity:
$ED_{50}$ = 8.7 mg/kg (s.c.) against E. coli SKF .12140 (cefazolin = 4.4 mg/kg)
(cefazolin = 0.70 mg/kg)
$ED_{50}$ = 0.7 mg/kg (s.c.) against K. pneumo. SKF 4200

EXAMPLE 55

7-(3-Aminomethylphenylacetamido)-3-(1-sulfomethyltetrazol-5-ylthiomethyl)-3-cephem-4-carboxylic acid Substitution of an equivalent amount of 3-aminomethylphenylacetic acid hydrochloride for 4-aminomethylphenylacetic acid hydrochloride in the reaction with 2-t-butoxycarbonyloxyimino-2-phenylacetonitrile described in Example 54 gave 3-(N-t-butoxycarbonylaminomethyl)phenylacetic acid, m.p. 95°–96.5°.

3-(N-t-butoxycarbonylaminomethyl)phenylacetic acid (3.47 g, 13 mmol) was dissolved in 115 ml of tetrahydrofuran and 1.8 ml (26 mmol) of triethylamine was added. The solution was cooled to −15° and 2 drops of N-methylmorpholine and 1.7 ml of i-butylchloroformate were added. The mixture was stirred for 20 minutes at −15° then a cold solution of 3.54 g (13 mmol) of 7-aminocephalosporanic acid in 70 ml of 50% aqueous tetrahydrofuran containing 1.8 ml of triethylamine was added while maintaining the temperature at −20° to −15°. The mixture was stirred for three hours then triethylamine was added to bring the pH to 7.0. Ethyl acetate (100 ml) was added, the mixture was acidified to pH 1.5 with 3 N hydrochloric acid, the layers were separated and the aqueous phase was re-extracted three times with ethyl acetate. The extracts were combined, dried ($MgSO_4$) and evaporated to give 7-(3-N-t-butoxycarbonylaminomethylphenylacetamido)cephalosporanic acid.

7-(3N-t-Butoxycarbonylaminomethylphenylacetamido)cephalosporanic acid was converted to the corresponding sodium salt by treatment with sodium 2-ethylhexanoate according to procedures described above.

A mixture of 0.812 g of 7-(3-N-t-butoxycarbonylaminomethylphenylacetamido)cephalosporanic acid sodium salt, 0.375 g of 1-sulfomethyltetrazole-5-thiol disodium salt and 0.131 g of sodium bicarbonate in 20 ml of water was heated and stirred at 55° for four hours while maintaining the pH at 6.8–7.0. The reaction mixture was cooled to ambient temperature, acidified to pH 1.5 with 3 N hydrochloric acid and extracted with ethyl acetate. The aqueous phase was adjusted to pH 6.8 with sodium carbonate and chromatographed on a XAD-7 resin column (pre-washed with water) using water as the eluant. The product containing fractions were combined and lyophilized to give 7-(3-N-t-butoxycarbonylaminomethylphenylacetamido)-3-(1-sulfomethyltetrazol-5-ylthiomethyl)-3-cephem-4-carboxylic acid disodium salt.

7-(3-N-t-Butoxycarbonylaminomethylphenylacetamido)-3-(1-sulfomethyltetrazol-5-ylthiomethyl)-3-cephem-4-carboxylic acid disodium salt was treated with trifluoroacetic acid as described above to give the title compound as the trifluoroacetate salt.

$C_{21}H_{22}F_3N_7O_9S_3$: Calculated: 37.67% C; 3.31% H; 14.64% N; Found: 37.28% C; 3.42% H; 14.85% N.

| In vitro activity: Bacteria | MIC (µg/ml) |
|---|---|
| Staph. aureus HH127 | 1.6 (0.4)* |
| Staph. aureus 671 | 6.3 (12.5) |
| Staph. aureus 674 | 1.6 (0.2) |
| Strep. faecalis HH 34358 | 100 (12.5) |
| E. coli SK&F 12140 | 1.6 (0.8) |
| E. coli 804 | >100 (100) |
| Kleb. pneumoniae SK&F 4200 | 0.2 (1.6) |
| Kleb. pneumoniae SK&F 1200 | ≦0.1 (0.8) |
| Kleb. pneumoniae 982 | >100 (>100) |
| Pseudo. aeruginosa HH63 | >100 (>100) |
| Pseudo. aeruginosa 647 | >100 (>100) |
| Serratia marcescens ATCC 13880 | >100 (>100) |
| Proteus morgani 179 | >100 (>100) |
| Proteus mirabilis 444 | 0.4 (3.1) |
| Enterobacter aerogenes | |

-continued

| In vitro activity: | |
|---|---|
| Bacteria | MIC (μg/ml) |
| 13048 | 50 (3.1) |
| *Enterobacter cloacae* | |
| 921 | 25 (6.3) |

*cefazolin

In vivo activity:

$ED_{50}$ = 1.82 mg/kg (s.c.) against *E. coli* SKF 12140 (cefazolin = 3.12 mg/kg)
$ED_{50}$ = <0.19 mg/kg (s.c.) against *K.pneumo.* pneumo. SK&F 4200 (cefazolin = 8.7 mg/kg)

EXAMPLE 56

An injectable pharmaceutical composition is formed by adding sterile water or sterile saline solution (2 ml.) to 500 mg. of 7-D-mandelamido-3-[1-(2-sulfamoylethyl)tetrazol-5-ylthiomethyl]-3-cephem-4-carboxylic acid sodium salt.

Pharmaceutical compositions of the other antibacterial compounds disclosed above may be formulated in a similar manner.

What is claimed is:

1. The compound 7-(3-aminomethylphenylacetamido)-3-(1-sulfomethyltetrazol-5-ylthiomethyl)-3-cephem-4-carboxylic acid or a non-toxic, pharmaceutically acceptable salt thereof.

2. A compound according to claim 1, said compound being 7-(3-aminomethylphenylacetamido)-3-(1-sulfomethyltetrazol-5-ylthiomethyl)-3-cephem-4-carboxylic acid trifluoroacetate salt.

3. The compound 7-(4-aminomethylphenylacetamido)-3-(1-sulfomethyltetrazol-5-ylthiomethyl)-3-cephem-4-carboxylic acid or a non-toxic, pharmaceutically acceptable salt thereof.

4. A compound according to claim 3, said compound being 7-(4-aminomethylphenylacetamido)-3-(1-sulfomethyltetrazol-5-ylthiomethyl)-3-cephem-4-carboxylic acid trifluoroacetate salt.

* * * * *